(12) United States Patent
Schacter et al.

(10) Patent No.: US 6,852,693 B2
(45) Date of Patent: Feb. 8, 2005

(54) COMPOSITIONS AND METHODS FOR PROMOTING LIPID MOBILIZATION IN HUMANS

(75) Inventors: Bernice Schacter, Wilmington, DE (US); Lee P. Schacter, Wilmington, DE (US)

(73) Assignee: BLM Group, Cambridge, MA (US)

( * ) Notice: Subject to any disclaimer, the term of this patent is extended or adjusted under 35 U.S.C. 154(b) by 0 days.

(21) Appl. No.: 10/072,419

(22) Filed: Feb. 7, 2002

(65) Prior Publication Data

US 2003/0162717 A1 Aug. 28, 2003

(51) Int. Cl.$^7$ .................. A61K 38/08; A61K 38/10; C07K 7/06; C07K 7/08

(52) U.S. Cl. ............... 514/13; 514/14; 514/15; 514/16; 530/326; 530/327; 530/328

(58) Field of Search .................. 514/12, 13, 14, 514/15, 16, 17; 530/300, 324, 325, 326, 327, 328, 329, 345

(56) References Cited

U.S. PATENT DOCUMENTS

| | | | |
|---|---|---|---|
| 4,260,601 A | 4/1981 | Reichelt et al. | 514/18 |
| 4,328,134 A | 5/1982 | Schally et al. | 525/54.11 |
| 4,464,356 A | 8/1984 | Mordes et al. | 424/573 |
| 4,489,059 A | 12/1984 | Rossini et al. | 424/573 |
| 4,891,219 A | 1/1990 | Karr, Jr. et al. | 424/145.1 |
| 5,219,579 A | 6/1993 | Tisdale et al. | 424/573 |
| 5,385,740 A | 1/1995 | Tisdale et al. | 424/573 |
| 5,830,994 A | 11/1998 | D'Hinteriand et al. | 530/300 |
| 6,344,441 B1 | 2/2002 | Bihain et al. | 514/12 |

OTHER PUBLICATIONS

GENBANK ® Database, Accession No. 7246026, Feb. 2, 1999.
GENBANK ® Database, Accession No. P25311, Aug. 20, 2001.
GENBANK ® Database, Accession No. XP_028425, Aug. 27, 2001.
GENBANK ® Database, Accession No. XP_028426, Aug. 27, 2001.
Beck, et al., Lipid mobilizing factors specifically associated with cancer cachexia, Br. J. Cancer, 63(6):846–850 (1991) (abstract only).
Beck, et al., Lipolytic factors associated with murine and human cancer cachexia, J. Natl. Cancer Inst., 82(24):1922–1926 (1990) (abstract only).
Fruebis et al., Proteolytic cleavage product of 30–kDa adipocyte complement–related protein increases fatty acid oxidation in muscle and causes weight loss in mice, PNAS, vol. 98, No. 4, pp. 2005–2010 (2001).

Gäde, Hyperprolinaemia caused by novel members of the adipokinetic hormone/red pigment–concentrating hormone family of peptides isolated from corpora cardiaca of onitine beetles, Biochem. J. 321:201–206 (1997).
Gäde, et al., Structure—Activity Relationships for *Periplaneta americana* Hypertrehalosemic Hormone I: The Importance of Side Chains and Termini, Peptides, vol. 16, No. 7, pp. 1173–1180 (1995).
Goldsworthy, et al., Structures, Assays and Receptors for Locust Adipokinetic Hormones, Comp. Biochem. Physiol., vol. 117B, No. 4, pp. 483–496 (1997).
Hayes, et al., Insect Hypertrehalosemic Hormone: Isolation and Primary Structure from *Blaberus discoidalis* Cockroaches, Biochemical and Biophysical Research Communications, vol. 140, No. 2, pp. 674–678 (1986).
Hirai, et al., Biological Evaluation of a Lipid–mobilizing Factor Isolated from the Urine of Cancer Patients, Cancer Research 58, 2359–2365 (1998).
Hollander, et al., Demonstration of lipolytic activity from cultured human melanoma cells, J. Surg. Res., 40(5): 445–449 (1986).
Inui, Cancer Anorexia–Cachexia Syndrome, Canser Research 59(18):4493–4501 (1999).
Kennedy, et al., Hydrophobic Ligand Binding by Zn–α$_2$–glycoprotein, a Soluble Fat–depleting Factor Related to Major Histocompatibility Complex Proteins, J. Biol. Chem. vol. 276, Issue 37, pp. 35008–35013 (2001) (abstract only).
Khan, et al., Catabolism of adipose tissue by a tumor–produced lipid mobilizing factor, Int. J. Cancer, 80(3):444–447 (1999) (abstract only).
Kitada, et al., Characterization of a lipid mobilizing factor from tumors, Prog. Lipid Res. 20:823–6 (1981) (abstract only).
Kitada, et al., Lipolysis induction in adipocytes by a protein from tumor cells, J. Cell Biochem., 20(4):409–16 (1982) (abstract only).
Knudtzon, et al., Acute in vivo stimulatory effects of human pituitary lipid–mobilizing factor on plasma levels of glucagon and insulin in rabbits, Horm. Metab. Res., 1:1–6 (1984) (abstract only).
Köllisch, et al., Structure elucidation and biological activity of an unusual adipokinetic hormone from corpora cardiaca of the butterfly, *Vanessa cardui*, Eur. J. Biochem. 267:5502–5508 (2000).

(List continued on next page.)

*Primary Examiner*—Jeffrey Edwin Russel
(74) *Attorney, Agent, or Firm*—Duane Morris LLP

(57) ABSTRACT

The invention provides methods of using polypeptide compounds based on the structures of insect peptides of the adipokinetic hormone family to mobilize lipids in humans. The compositions and methods described in the application are useful for modulating human body weight, such as inducing weight loss. The invention also includes screening methods for identifying other compounds effective for modulating lipid mobilization in humans.

54 Claims, No Drawings

OTHER PUBLICATIONS

Lewis, et al., Hypertrehalosemic hormone in a cockroach: molecular cloning and expression, Molecular and Cellular Endocrinology, 130:101–108 (1997).

Lorenz, et al., Hypertrehalosemic peptides in the honeybee (*Apis mellifera*): purification, identification, and function, J. insect Phy. 45:647–653 (1999).

McDevitt, et al., Purification and Characterization of a Lipid–mobilizing Factor Associated with Cachexia–inducing Tumors in Mice and Humans, Cancer Research, 55:1458–1463 (1995).

Osuga, et al., Targeted disruption of hormone–sensitive lipase results in male sterility and adipocyte hypertrophy, but not in obesity, PNAS, vol. 97, Issue 2, pp. 787–792 (2000).

Price, et al., Mechanism of inhibition of a tumor lipid–mobilization factor by eicosapentaenoic acid, Cancer Research, vol. 58, Issue 21, 4827–4831 (1998).

Raina, et al., Primary Structure of a Novel Neuropeptide Isolated from the Corpora Cardiaca of Periodical Cicadas Having Adipokinetic and Hypertrehalosemic Activities, Insect Biochem Mol. Biol., vol. 25, No. 8, pp. 929–932 (1995).

Richter, et al., Peptide hormones and lipolysis in rabbit adipocytes, Horm. Metab. Res., 17(3):127–30 (1985) (abstract only).

Richter, et al., Lipolytic potency of proopiomelanocorticotropin peptides in vitro, Neuropeptides, 9(1):59–74 (1987) (abstract only).

Richter, et al., On the in vitro lipolytic activity of peptide hormones in human adipose tissue, Horm. Metab. Res. Suppl., 19:44–49 (1998) (abstract only).

Roeder, Octopamine in Invertebrates, Progress in Neurobiology, vol. 59, pp. 533–561 (1999).

Saltiel, Another hormone–sensitive triglyceride lipase in fat cells?, PNAS, vol. 97, Issue 2, pp. 535–537 (2000).

Sanchez, et al., Crystal Structure of Human ZAG, a FatDepleting Factor Related to MHC Molecules, Science, vol. 283, pp. 1914–1919 (1999).

Sasek, et al., An antiserum to locust adipokinetic hormone reveals a novel peptidergic system in the rat central nervous system, Brain Research, 343:172–175 (1985).

Schueler, et al., Identification and Initial Characterization of Adipokinetic Hormone–Like Immunoreactive Peptides of Rat Origin, Journal of Neuorochemistry, pp. 133–138 (1986).

Siegert, et al., Locust corpora cardiaca contain an inactive adipokinetic hormone, FEBS Letters, 447:237–240 (1999).

Stone, et al., Structures of locust adipokinetic hormone, a neurohormone that regulates lipid utilisation during flight, Nature, 263(5574):207–211 (1976) (abstract only).

Suzuki, et al., Identification and Characterization of Adipokinetic Hormone (Locusta Migratoria)–Like Immunoreactivity in the Human Cerebrospinal Fluid, Biochem. and Biophys. Res. Commun., vol. 163, No. 1, pp. 534–540 (1989).

Taylor, et al., Identification of a Human Tumor–derived Lipolysis–promoting Factor, Cancer Research, 52:829–834 (1992).

Thompson, et al., Increased expression of the mRNA for hormone–sensitive lipase in adipose tissue of cancer patients, Biochemica et. Biophysica Acta, 1180:236–242(1993).

Tisdale, Cancer cachexia, Anticancer Drugs, 4(2):115–125 (1993) (abstract only).

Tisdale, et al., Cancer anorexia and cachexia, Nutrition, 17(5):438–442 (2001).

Todorov, et al., Induction of muscle protein degradation and weight loss by a tumor product, Cancer Research, 56(6):1256–1261 (1996) (abstract only).

Todorov, et al., Purification and characterization of a tumor lipid–mobilizing factor, Cancer Research, 58(11) 2353–2358 (1998) (abstract only).

Todorov, et al., Structural Analysis of a Tumor–produced Sulfated Glycoprotein Capable of Initiating Muscle Protein Degradation, J. Biol. Chem., vol. 272, No. 19, pp. 12279–12288 (1997).

Velentza, et al., Synthesis and biological activity of adipokinetic hormone analogues with modifications in the 4–8 region, Peptides, 21:631–637 (2000).

Ziegler, et al., Analogs of *Manduca* Adipokinetic Hormone Tested in Bioassay and in a Receptor–Binding Assay, Peptides, vol. 19, No. 3, pp. 481–486 (1998).

Jaffe et al., 1986, Biochem. Biophys. Res. Commun. 135 (2) 622–628 (abstract only).

Jaffe et al., 1988, Biochem. Biophys. Res. Commun. 155 (1) 344–350 (abstract only).

Jaffe et al., 1989, Proc. Natl. Acad. Sci. USA 86: (20):8161–8164 (abstract only).

COMPOSITIONS AND METHODS FOR PROMOTING LIPID MOBILIZATION IN HUMANS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

Obesity and less severe overweight conditions are a significant cause of morbidity and mortality in humans. High body weight is a risk factor for many diseases and disorders, particularly when fat comprises a high percentage of body weight. For example, incidence of each of type II diabetes, cholelithiasis, hypertension, and coronary heart disease is much greater in obese humans than in non-obese humans. Other diseases associated with obesity include arthritis, various cancers (e.g., breast, colorectal, and endometrial cancers), renal failure, liver disease, chronic pain (e.g., lower back pain), sleep apnea, stroke, and urinary incontinence.

In addition to medical risks attributable to large amounts of body fat, fat accumulation is considered by many to be cosmetically undesirable as well. Likely attributable to popular notions regarding desirable body size and shape, many people are afflicted by psychological disruptions that might be alleviated if body fat were reduced or more easily controlled.

Body mass index (BMI) is a common measurement used to diagnose overweight and obesity. BMI is calculated by dividing an individual's weight in kilograms by the square of the individual's height in meters. Weight classifications have been developed by the National Heart, Lung, and Blood Institute (NHLBI), and these classifications can be used to divide the population into six groups, based on BMI, as follows:

| Classification | BMI (body weight in kilograms per square of height in meters) |
| --- | --- |
| Underweight | <18.5 |
| Normal | 18.5 to <25.0 |
| Overweight | 25.0 to <30.0 |
| Obesity Class 1 | 30.0 to <35.0 |
| Obesity Class 2 | 35.0 to <40.0 |
| Obesity Class 3 | ≧40.0 |

Using the NHLBI criteria, 17.9% of the U.S. population was obese (obesity class 1, 2, or 3) in 1998, corresponding to more than 45 million individuals. Estimates of medical costs attributable to obesity and related conditions were about $100 billion in the United States in 1999 (American Obesity Association report, 1999, "Costs of Obesity"). Furthermore, significant costs are associated with weight loss programs undertaken by individuals (e.g., about $33 billion per year in the U.S. in the late 1990s; 1998 Federal Trade Commission Report, "Consumer Weight Loss Products and Programs").

Clearly, obesity and overweight are problems of critical importance. Significant economic, medical, and psychological gains could be achieved if compositions and methods could be developed that allow people to lose weight.

Prior art weight loss methods and compositions have not been widely successful. Current treatments for obesity and overweight include diet, pharmaceutical agents, surgery, and herbal therapy. Dietary methods for inhibiting or reversing obesity and overweight have a very low long term benefit rate. Although some pharmaceutical agents (and combinations of agents) have exhibited the ability to reduce body weight, many of these agents have been withdrawn from markets owing to toxicity, lack of efficacy, or both. Surgical methods of treating obesity and overweight are costly, are sometimes accompanied by very serious complications, exhibit significant variation in outcome, and are not amenable for use in all patients. Herbal (and "nutraceutical") compositions for weight loss are popular, but their efficacy is typically not demonstrated. Owing to their often unknown mechanism of action, the variability of their composition, and their lack of credible clinical data, herbal weight loss compositions are not suitable for widespread use in the population.

A critical need remains for compositions and methods that can be used to effect weight loss in humans. The present invention satisfies this need, at least in part, by providing such compositions and methods.

BRIEF SUMMARY OF THE INVENTION

The invention relates to a method of promoting lipid mobilization (e.g., for the purpose of effecting weight loss, suppressing appetite, or both) in a human. The method comprises administering an insect adipokinetic hormone (AKH) to the human in an amount (e.g., 100 milligrams to 2 grams per day) effective to mobilize lipids in the human. Among the useful insect AKHs are those which exhibit one or more of the following characteristics: i) it has a molecular weight less than 2500; ii) it is a polypeptide having a pyroglutamate residue at its amino terminus; iii) it is a polypeptide having a blocked (e.g., aminated or amidated) carboxyl terminus; iv) it is a polypeptide that does not have internal disulfide bonds, and v) its ability to promote lipid mobilization is not significantly inhibited by propanolol.

In one embodiment, the AKH is a polypeptide compound having the chemical structure

$Xaa^1\text{-}Xaa^2\text{-}Xaa^3\text{-}Xaa^4\text{-}Xaa^5\text{-}Xaa^6\text{-}Xaa^7\text{-}Xaa^8\text{-}X\text{-}Z$, wherein:

$Xaa^1$ is a pyroglutamate residue;

$Xaa^2$ is one of a leucine residue, an isoleucine residue, a valine residue, a phenylalanine residue, and a tyrosine residue (preferably either leucine or valine residue);

$Xaa^3$ is one of an asparagine residue and a threonine residue;

$Xaa^4$ is one of a phenylalanine residue and a tyrosine residue (preferably phenylalanine);

$Xaa^5$ is one of a threonine residue and a serine residue;

$Xaa^6$ is one of a proline residue, a serine residue, a threonine residue, and an alanine residue (preferably proline, serine, or threonine);

$Xaa^7$ is one of glycine residue, an asparagine residue, a serine residue, an aspartate residue, a valine residue, and a tryptophan residue (preferably glycine, asparagine, or serine);

$Xaa^8$ is a tryptophan residue;

X is from 0 to 10 amino acid residues (preferably 0 to 3; more preferably 0); and Z is one of a hydrogen radical and a carboxyl terminus-blocking moiety (preferably an (—$NH_2$) radical).

In some embodiments, it is preferred that the carboxyl terminus amino acid residue of the polypeptide compound is a glycine residue, in order to facilitate amidation of the carboxyl terminus in vivo. In the structure, X can have the chemical structure $$Xaa^9\text{-}Xaa^{10}\text{-}Xaa^{11}\text{-}(Xaa^{12})_n$$

wherein:

n is from 0 to 7;

$Xaa^9$ is glycine;

$Xaa^{10}$, when present, is one of a threonine residue, a glycine residue, a tryptophan residue, a serine residue, and an asparagine residue (preferably threonine); and $Xaa^{11}$, when present, is a lysine residue; and each $Xaa^{12}$, when present, is independently any amino acid residue.

In another embodiment, the polypeptide compound has the chemical structure $$Xaa^1\text{-}Xaa^{22}\text{-}Xaa^{23}\text{-}Xaa^{24}\text{-}Xaa^{25}\text{-}Xaa^{26}\text{-}Xaa^{27}\text{-}Xaa^{28}\text{-}X\text{-}Z,$$

wherein:

$Xaa^1$ is a pyroglutamate residue;

$Xaa^{22}$ is an amino acid residue having a non-polar side chain;

$Xaa^{23}$ is an amino acid residue having a non-ionic polar side chain;

$Xaa^{24}$ is an amino acid residue having an aromatic side chain;

$Xaa^{25}$ is an amino acid residue having a non-ionic polar side chain;

$Xaa^{26}$ is any amino acid residue (preferably proline, serine, threonine, or alanine);

$Xaa^{27}$ is any amino acid residue (preferably glycine, asparagine, serine, glutamate, valine, or tryptophan;

$Xaa^{28}$ is an amino acid residue having an aromatic side chain;

X is from 0 to 10 amino acid residues (preferably either 0 or glycine); and

Z is one of a hydrogen radical and a carboxyl terminus blocking moiety (preferably an (—$NH_2$) radical, unless X is glycine, in which event Z is preferably a hydrogen radical).

The polypeptide compound can be a polypeptide having an amino acid selected from the group consisting of SEQ ID NOs: 1–40, wherein the amino-terminal glutamate residue of the polypeptide is a pyroglutamate residue, and wherein the carboxyl terminal residue of the polypeptide is amidated. Alternatively, the polypeptide compound can be 6 or 7 amino acid residues in length and have the chemical structure of either of formulas IV and V disclosed herein.

Lipid mobilization can be promoted in a human either by administering a polypeptide compound described herein (or a variant of such a polypeptide compound) to the human, or by administering to the human a nucleic acid expression vector comprising a nucleic acid that encodes such a polypeptide compound.

BRIEF DESCRIPTION OF THE SEVERAL VIEWS OF THE DRAWINGS

Not applicable.

DETAILED DESCRIPTION OF THE INVENTION

The invention relates to polypeptide-based compounds for mobilizing lipids in humans, including in human adipocytes. The compounds can be used to effect weight loss in humans. Owing to this activity, the compounds can be used to alleviate, inhibit, or reverse obesity and overweight in humans. The polypeptide-based compounds that can be used for these purposes include insect adipokinetic hormones (AKHs) and AKHs that are derivatized by known polypeptide derivatization methods and that retain lipid mobilizing activity in humans. The invention includes methods, pharmaceutical compositions, kits, and screening methods relating to these compounds.

Definitions

As used herein, each of the following terms has the meaning associated with it in this section.

An "obese" human is a human having a BMI≧30.0, which includes humans classified in one of the obesity class 1, 2, and 3 categories of the NHLBI weight classification system.

An "overweight" human is a human having a BMI≧25.0 and <30.0, which includes humans classified in the overweight category of the NHLBI weight classification system.

An "insect adipokinetic hormone" means an adipokinetic hormone (AKH) that occurs naturally in an organism in Class Insecta, Subphylum Uniramia, and Phylum Arthropoda. Insect AKHs have chemical structures that are identical to color change hormones of various decapod crustaceans, such as the red pigment concentrating hormone isolated from prawn eye stalks (see Fernlund et al., 1972, Science 177:173–175). Hence, these decapod crustacean pigment concentrating hormones are also considered insect AKHs for the purposes of this disclosure.

An "adipokinetic hormone" ("AKH") means any polypeptide hormone in the class of polypeptide hormones recognized as AKHs, regardless of the name applied to the hormone. By way of example, the AKH family of polypeptide hormones includes hormones designated AKH, AKH I, AKH II, hypertrehalosemic factor, hypertrehalosemic neuropeptide, hypertrehalosemic peptide (HTP), and red or yellow pigment concentrating hormones.

"Lipolysis" refers to decomposition or hydrolysis of fats (i.e., lipids) into components thereof. By way of example, hydrolysis of an acyl glyceride results in cleavage of the ester bond between one or more carboxylic acid moieties of the glyceride and the glycerol moiety of the glyceride.

"Mobilization" of lipids refers to release from a lipid-containing cell (e.g., an adipocyte) of a lipid that is normally stored therein, lipolysis of the lipid, or both. Mobilization can include transfer of the lipid from the interior to the exterior of the cell in a modified form or in an unmodified form.

A "pharmaceutically acceptable carrier" means a chemical composition with which a biologically active ingredient can be combined and which, following the combination, can be used to administer the active ingredient to a human.

A "physiologically acceptable" ester or salt means an ester or salt form of the active ingredient which is compatible with any other ingredients of the pharmaceutical composition and which is not deleterious to the human to which the composition is to be administered.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked with the coding region of a gene is able to promote transcription of the coding region.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a constitutive, inducible, or tissue specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living human cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

Detailed Description

The invention is based on the discovery that insect AKHs and their derivatives can be used to mobilize lipids in humans and other mammals. This discovery is surprising, given the evolutionary distance between humans and insects (whose latest common evolutionary ancestors are believed to be flatworms). The data disclosed herein indicate that the genus and species of the insect is not critical, and that AKHs from a variety of different insects will exhibit the ability to mobilize lipids in humans. Furthermore, it is recognized that known methods can be used to derivatize insect AKHs in order to yield peptides which exhibit improved pharmacological properties (e.g., decreased immune response or decreased rate of degradation in vivo), and methods of screening such derivatives in order to identify such improved peptides are included in the invention.

Mobilization of lipids inhibits or prevents their storage, and promotes depletion of lipid stores. Mobilization of lipids from adipocytes increases the ability of lipids and lipid components to be taken up into the bloodstream and carried to portions of the body where they can be metabolized, transformed, or excreted. Thus, lipid mobilization permits at least partial depletion of lipid stores. Depletion of lipid stores is beneficial, for example for promoting weight loss and for enhancing metabolic availability of lipids (e.g., in humans experiencing an interruption in normal lipid metabolism.

The appetite urge experienced by humans is related in ways that are not thoroughly understood to the concentration of lipids and lipid components (e.g., fatty acids) in the bloodstream. Because the compositions and methods described herein can increase blood levels of lipids and their components, appetite can be suppressed in a human using those compositions and methods to mobilize lipids. Thus, the compositions and methods described herein can be used to decrease lipid stores, to limit appetite, or both.

Excess lipid storage is associated with a variety of undesirable conditions and disorders. For example, fat accumulation can cause cosmetically undesirable body shape and size, and can increase the incidence of various disorders. Examples of these disorders include obesity, overweight, type II diabetes, cholelithiasis, hypertension, coronary heart disease, arthritis, various cancers (e.g., breast, colorectal, and endometrial cancers), renal failure, liver disease, chronic pain (e.g., lower back pain), sleep apnea, stroke, and urinary incontinence. A patient afflicted with one or more of these conditions or disorders can use the compositions and methods described herein to alleviate, reverse, or eliminate the condition or disorder. A patient at risk for developing one of these conditions or disorders can use the compositions and methods described herein to inhibit or prevent its occurrence.

Atherosclerosis is a condition wherein deposits containing cholesterol, lipid materials, and lipid laden macrophages accumulate on and in the intimal and inner medial layers of arteries. Prolonged or excessive atherosclerosis can lead to thickening and loss of elasticity of arterial walls, to chronic ischemic disorders, to chronic thrombotic disorders, or to combinations of these. The compositions and methods described herein can be used to inhibit or prevent development and growth of atherosclerotic deposits or to diminish the size or extent of existing deposits. Owing to this capability, the methods and compositions described herein can inhibit or alleviate conditions and disorders attributable, at least in part to atherosclerosis. Examples of these disorders include high blood pressure, coronary artery disease, cardiac insufficiency, and stroke. It is not necessary that atherosclerotic deposits be detected in a patient before administering a composition comprising an insect AKH to the patient. Instead, the composition can be administered as part of a normal diet, as part of a diet prescribed for a person who exhibits abnormally high systemic cholesterol or lipid levels, or to a patient who is believed for some other reason to be at risk for developing atherosclerosis. Without being bound by any particular theory of operation, it is believed that the compositions and methods described herein induce or enhance mobilization of lipids from lipid-laden macrophages, and that the compositions and methods can also induce or enhance lipolysis of lipid materials in atherosclerotic deposits.

The AKHs and AKH derivatives described herein can be administered to a human alone (i.e., in a formulation containing only the AKH or derivative), or it can be combined with, contained in, or admixed with one or more active ingredients or pharmaceutically acceptable carriers.

Substantially any insect AKH can be used. Examples of insects in which AKHs have been described are listed in Table 1, together with references that describe them. More than one AKH has been described for several of the insects in Table 1, and any of those AKHs can be used as described herein. Amino acid sequences of suitable AKHs are listed in Table 2. The amino-terminal glutamate residue of each of the sequences listed in Table 2 is a pyroglutamate (cyclized glutamate or glutamine) residue, and the carboxyl-terminal residue of each of the sequences can be (and preferably is) an amide form of the residue (e.g., an aminated residue made by adding an amino {—NH₂} radical to the carboxy terminus to form the corresponding amide). The amino acid sequence, presence of an amino-terminal pyroglutamate residue, and presence of carboxyl-terminal amidation in AKHs that have been described by others for the organisms listed in Table 1 are listed in Table 3.

TABLE 1

| Common Name | Genus, species name | Reference |
|---|---|---|
| Desert Locust | Schistocera gregaria | Nature 263: 207–211, 1976; Experimentia 48(5): 430–438, 1992; J. Neuro. Sci. 9: 996–1003, 1989 |
| Migratory Locust | Locusta migratoria | Nature 263: 207–211 1976; Biol. Chem. Hoppe Seyler 366(8): 723–727, 1985; Eur. J. Biochem. 195(2): 351–359, 1991 |
| Honey bee | Apis mellifera | J. Insect Phys. 45: 647–653, 1999; Biochem. Biophys. Res. Comm. 133(1): 337–342, 1985 |
| Dragonfly | Libellula auripennis | Biol. Chem. Hoppe Seyler 371 (6): 475–483 1990 |
| Emperor dragonfly | Anax imperator | Peptides 15(1): 1–6, 1994 |
| Damselfly | Pseudagrion inconspicuum | Biochem. J. 302: 539–543, 1994 |
| Damselfly | Ishnura senegalensis | Biochem. J. 302: 539–543, 1994 |
| Sawfly | Tenthredo arcuata | J. Insect Physiol. 47(6): 563–571, 2001 |
| Fruit fly | Drosophila melanogaster | Biochem. J. 269(2): 315–320, 1990 |
| Horse fly | Tabanus atratus | Proc. Natl. Acad. Sci. USA 86: 8161–8164, 1989 |
| Blowfly | Phormia terraenova | Biochem. J. 269(2): 309–312, 1990 |
| Butterfly | Vanessa cardui | Eur. J. Entomol. 96(3): 309–315, 1999; Eur. J. Biochem. 267: 5502–5508, 2000 |
| Tobacco hornworm moth | Manduca sexta | J. Insect Phys. 45: 647–653, 1999; Biochem. Biophys. Res. Comm. 133(1): 337–342, 1985 |
| Beetle | Melolontha melolontha | Biochem. J. 275: 671–677, 1991 |
| Beetle | Geotrupes stercorosus | Biochem. J. 275: 671–677 1991 |
| Onitine beetle | Onitis sp. | Biochem. J. 321: 201–206, 1997 |
| Tenebrionid beetle | Tenebrio molitor | Peptides 11(3): 455–459, 1990 |
| Tenebrionid beetle | Zophobas rugipes | Peptides 11(3): 455–459, 1990 |
| Dung Beetle | Scarabaeus sp. | Biochem. Biophys. Res. Commum. 230(1): 16–21, 1997 |
| Grasshopper | Phymateus leprosus | Reg. Peptides 57(3): 247–252, 1995 |
| Grasshopper | Melanoplus sanguinipes | Biochem. Biophys. Res. Comm. 239: 763–768, 1997 |
| African pyrgomorphid grasshopper | Dictyophorus spumans | Insect Biochem. Mol. Biol. 30(11): 1061–1067, 2000 |
| African pyrgomorphid grasshopper | Phymateus morbillosus | Insect Biochem. Mol. Biol. 30(11): 1061–1067, 2000 |
| Cricket | Gryllodes sigillatus | Biol. Chem. Hoppe Seyler 373(11): 1169–1178, 1992 |
| King cricket | Libanasidus vittatus | Biol. Chem. Hoppe Seyler 373(11): 1169–1178, 1992 |
| Ground cricket | Heterodes namaqua | Biol. Chem. Hoppe Seyler 373(11): 1169–1178, 1992 |
| Ground cricket | Acanthoproctus cervinus | Biol. Chem. Hoppe Seyler 373(11): 1169–1178, 1992 |
| American cockroach | Periplaneta americana | Peptides 16(7): 1173–1180 1995 |
| Cockroach | Leucophaea maderae | Biol. Chem. Hoppe Seyler 371(4): 345–354, 1990 |
| Cockroach | Gromphadorhina portentosa | Biol. Chem. Hoppe Seyler 371(4): 345–354, 1990 |

TABLE 1-continued

| Common Name | Genus, species name | Reference |
|---|---|---|
| Cockroach | Blattella germanica | Biol. Chem. Hoppe Seyler 371(4): 345–354, 1990 |
| Cockroach | Blatta orientalis | Biol. Chem. Hoppe Seyler 371(4): 345–354, 1990 |
| Tropical cockroach | Blaberus discoidalis | Biochem. Biophys. Res. Comm. 140: 674–678, 1986; Biol. Chem. Hoppe Seyler 371(4): 345–354, 1990 |
| Primitive cockroach | Polyphaga aegyptiaca | Gen. Comp. Endocrinol. 86(1): 119–127, 1992 |
| Mantid | Empusa pennata | Biol. Chem. Hoppe Seyler 372(3): 193–201, 1991 |
| Periodical cicadas | Platypleura capensis Cacama valavata Diceroprocta semicinta | Insect Biochem. Mol. Biol. 25(8): 929–932, 1995; Biol. Chem. Hoppe Seyler 375: 803–809, 1994; Arch. Insect Biochem. Physiol. 29(4): 391–396, 1995 |
| Stick Insect | Extatosoma tiaratum | Biol. Chem. Hoppe-Seyler 67: 368, 1987 |
| Firebug | Pyrrhocoris apterus | Insect Biochem. Mol. Biol. 30(6): 489–498, 2000 |
| Corn ear worm | Heliothis zea | Biochem. Biophys. Res. Comm. 135: 622–628, 1986; Biochem. Biophys. Res. Comm. 155: 334–350, 1988 |

TABLE 2

| Amino Acid Sequence | SEQ ID NO: | Amino Acid Sequence | SEQ ID NO: |
|---|---|---|---|
| ELNFTPNWGT | 1 | ELNFSPNW | 21 |
| EVNFSPGWGT | 2 | EITFTPNW | 22 |
| ELNFSTGW | 4 | EVNFTPNW | 23 |
| ELTFTSSWG | 3 | EVNFSTGW | 24 |
| EVNFTPGW | 5 | ELNFSTGW | 25 |
| ELTFSPDW | 6 | EVNFTPGW | 26 |
| ELTFSPDW | 7 | EINFTPWW | 27 |
| ELTFTSSWG | 8 | EFNYSPDW | 28 |
| ELNFTPNW | 9 | EFNYSPVW | 29 |
| ELNFTPWW | 10 | EYNFSTGW | 30 |
| ELNFSAGW | 11 | EFNYSPDW | 31 |
| EVNFSPNW | 12 | EVNFSPSWGN | 32 |
| ELNYSPDW | 13 | ELTFTPNWGT | 33 |
| ELTFTPGW | 14 | ELTFSSGWGN | 34 |
| ELNFSTGW | 15 | ELNFTPNWGT | 35 |
| EVNFTPSW | 16 | ELNFSTGWGG | 36 |
| EVNFSPSW | 17 | ELTFTSSWGGK | 37 |
| EVNFSPNW | 18 | ELTFTPNW | 38 |
| ELTFTPNW | 19 | ELTFTPNWGS | 39 |
| ELNFSPNW | 20 | ELTFTPGWGY | 40 |

TABLE 3

| Common Name | Genus, species name | Amino Acid Sequence (SEQ ID NO:) | N-Terminal pyroGlu residue? | C-Terminal amination? |
|---|---|---|---|---|
| Desert Locust | Schistocera gregaria | 1 | X | X |
| Desert Locust | Schistocera gregaria | 4 | X | X |
| Desert Locust | Schistocera gregaria | 4 | X | X |
| Desert Locust | Schistocera gregaria | 35 | X | X |
| Migratory Locust | Locusta migratoria | 1 | X | X |
| Migratory Locust | Locusta migratoria | 10 | X | X |

TABLE 3-continued

| Common Name | Genus, species name | Amino Acid Sequence (SEQ ID NO:) | N-Terminal pyroGlu residue? | C-Terminal amination? |
|---|---|---|---|---|
| Migratory Locust | Locusta migratoria | 11 | X | X |
| Honey bee | Apis mellifera | 3 | X | X |
| Dragonfly | Libellula auripennis | 16 | X | X |
| Emperor dragonfly | Anax imperator | 17 | X | X |
| Damselfly | Pseudagrion inconspicuum | 5 | X | X |
| Damselfly | Pseudagrion inconspicuum | 26 | X | X |
| Damselfly | Ishnura senegalensis | 26 | X | X |
| Sawfly | Tenthredo arcuata | 36 | X | |
| Fruit fly | Drosophila melanogaster | 6 | X | X |
| Horse fly | Tabanus atratus | 14 | X | X |
| Horse fly | Tabanus atratus | 40 | X | X |
| Blowfly | Phormia terraenova | 7 | X | X |
| Butterfly | Vanessa cardui | 8 | X | X |
| Butterfly | Vanessa cardui | 37 | X | No |
| Tobacco hornworm moth | Manduca sexta | 3 | X | X |
| Beetle | Melolontha melolontha | 13 | X | X |
| Beetle | Geotrupes stercorosus | 13 | X | X |
| Onitine beetle | Onitis sp. | 30 | X | X |
| Onitine beetle | Onitis sp. | 31 | X | X |
| Tenebrionid beetle | Tenebrio molitor | 20 | X | X |
| Tenebrionid beetle | Zophobas rugipes | 20 | X | X |
| Dung Beetle | Scarabaeus sp. | 28 | X | X |
| Dung Beetle | Scarabaeus sp. | 29 | X | X |
| Grasshopper | Phymateus leprosus | 15 | X | X |
| Grasshopper | Melanoplus sanguinipes | 1 | X | X |
| African pyrgomorphid grasshopper | Dictyophorus spumans | 27 | X | X |
| African pyrgomorphid grasshopper | Phymateus morbillosus | 27 | X | X |
| Grasshopper | Phymateus leprosus | 39 | X | X |
| Cricket | Gryllodes sigillatus | 24 | X | X |
| King cricket | Libanasidus vittatus | 25 | X | X |
| Ground cricket | Heterodes namaqua | 25 | X | X |
| Ground cricket | Acanthoproctus cervinus | 25 | X | X |
| American cockroach | Periplaneta americana | 12 | X | X |
| American cockroach | Periplaneta americana | 38 | X | X |
| Cockroach | Leucophaea maderae | 38 | X | X |
| Cockroach | Leucophaea maderae | 38 | X | X |
| Cockroach | Grompha-dorhina portenetosa | 2 | X | X |
| Cockroach | Grompha-dorhina portenetosa | 2 | X | X |
| Cockroach | Blattella germanica | 2 | X | X |
| Cockroach | Blatta orientalis | 18 | X | X |
| Cockroach | Blatta orientalis | 19 | X | X |
| Tropical cockroach | Blaberus discoidalis | 2 | X | X |
| Primitive cockroach | Polyphaga aegyptiaca | 21 | X | X |
| Primitive cockroach | Polyphaga aegyptiaca | 22 | X | X |
| Mantid | Empusa pennata | 23 | X | X |
| Periodical cicadas | Platypeleura capensis Cacama valavata Diceroprocta semicinta | 32 | X | X |
| Stick Insect | Extatosoma tiaratum | 33 | X | X |
| Firebug | Pyrrhocoris apterus | 9 | X | X |
| Corn ear worm | Heliothis zea | 3 | X | X |
| Corn ear worm | Heliothis zea | 34 | X | X |

Each of the polypeptide AKHs described in Tables 2 and 3 can be used in the compositions and methods described herein. Other polypeptides that can be used are those having the chemical structure shown in formula I:

$$Xaa^1\text{-}Xaa^2\text{-}Xaa^3\text{-}Xaa^4\text{-}Xaa^5\text{-}Xaa^6\text{-}Xaa^7\text{-}Xaa^8\text{-}X\text{-}Z \qquad (I).$$

In formula I:

$Xaa^1$ is a pyroglutamate residue;

$Xaa^2$ is one of a leucine residue, an isoleucine residue, a valine residue, a phenylalanine residue, and a tyrosine residue (preferably a leucine or valine residue);

$Xaa^3$ is one of an asparagine residue and a threonine residue;

$Xaa^4$ is one of a phenylalanine residue and a tyrosine residue (preferably a phenylalanine residue);

$Xaa^5$ is one of a threonine residue and a serine residue;

$Xaa^6$ is one of a proline residue, a serine residue, a threonine residue, and an alanine residue (preferably not alanine);

$Xaa^7$ is one of glycine residue, an asparagine residue, a serine residue, an aspartate residue, a valine residue, and a tryptophan residue (preferably a glycine, asparagine, or serine residue);

$Xaa^8$ is a tryptophan residue;

X is from 0 to 10 amino acid residues (preferably 0 to 3, and more preferably 0); and Z is one of a hydrogen radical and a carboxyl terminus-blocking moiety (preferably an (—$NH_2$) radical).

When the moiety designated X in formula I is 1 to 10 amino acid residues, it preferably has the chemical structure shown in formula II:

$$Xaa^9\text{-}Xaa^{10}\text{-}Xaa^{11}\text{-}(Xaa^{12})_n \qquad (II).$$

In formula II, n is from 0 to 7 (preferably 0)

Xaa⁹ is a glycine residue,

Xaa¹⁰, when present, is one of a threonine residue, a glycine residue, a tryptophan residue, a serine residue, and an asparagine residue (preferably a threonine residue);

Xaa¹¹ when present, is a lysine residue; and each Xaa ¹², when present, is any amino acid residue.

The polypeptide compounds that can be used as described herein can have lengths from 8 to about 18 amino acid residues, and preferably have an overall molecular weight less than 2,500. It is recognized that smaller peptide compounds are generally better able to pass through biological membranes than larger peptide compounds. Thus, when a compound described herein is administered by a route that requires passage across a biological membrane or cell layer (e.g., when administered by an oral route), it is preferred that shorter polypeptide compounds be used.

The polypeptide compounds useful as described herein are not limited to those that are explicitly disclosed herein, but instead include conservative variants and derivatives of the sort that are routinely made by those skilled in the art. For example, conservative amino acid changes may be made, which although they alter the primary sequence of the protein or peptide, do not eliminate its biological activity. Conservative amino acid substitutions typically include substitutions within the following groups:

glycine, alanine;

valine, isoleucine, leucine;

aspartic acid, glutamic acid;

asparagine, glutamine;

serine, threonine;

lysine, arginine;

phenylalanine, tyrosine.

Appropriate amino acid residue substitutions can also be made by replacing a residue with another residue having the same type of side chain. For example, amino acid residues having non-polar side chains (e.g., leucine, isoleucine, valine, phenylalanine, alanine, and glycine residues), non-ionic polar side chains (e.g., asparagine, glutamine, serine, and threonine residues), and aromatic side chains (e.g., phenylalanine, tyrosine, tryptophan, and histidine residues) can be interchanged. Other suitable derivatization procedures include acetylation, phosphorylation, esterification, and carboxylation of amino acid side chain moieties. Similarly, the polypeptide compound can be pegylated (polyethylene glycol-substituted), encapsulated or incorporated into a liposome, or linked with a fatty acid such as docosahexanoic acid. The biological activity of substituted or derivatized polypeptide compounds can be assessed using the screening methods described herein.

Another class of polypeptides that can be used are those which have the chemical structure shown in formula III:

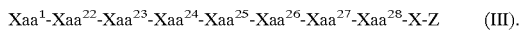

Xaa¹-Xaa²²-Xaa²³-Xaa²⁴-Xaa²⁵-Xaa²⁶-Xaa²⁷-Xaa²⁸-X-Z     (III).

In formula III,

Xaa²² is an amino acid residue having a non-polar side chain;

Xaa²³ is an amino acid residue having a non-ionic polar side chain;

Xaa²⁴ is an amino acid residue having an aromatic side chain;

Xaa²⁵ is an amino acid residue having a non-ionic polar side chain;

Xaa²⁶ is any amino acid residue;

Xaa²⁷ is any amino acid residue;

Xaa²⁸ is an amino acid residue having an aromatic side chain; and

Xaa¹, X, and Z have the identities described above.

In some embodiments, the polypeptide compounds can have lengths even shorter than 8 amino acid residues (e.g., compounds 6 or 7 residues in length). When the compound has a length of 7 amino acid residues, it preferably has the chemical structure shown in formula IV:

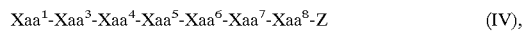

Xaa¹-Xaa³-Xaa⁴-Xaa⁵-Xaa⁶-Xaa⁷-Xaa⁸-Z     (IV), wherein Xaa¹, Xaa³, Xaa⁴, Xaa⁵, Xaa⁶, Xaa⁷, Xaa⁸, and Z have the identities described above. When the compound has a length of 6 amino acid residues, it preferably has the chemical structure shown in formula V:

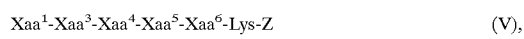

Xaa¹-Xaa³-Xaa⁴-Xaa⁵-Xaa⁶-Lys-Z     (V), wherein Xaa¹, Xaa³, Xaa⁴, Xaa⁵, Xaa⁶, and Z have the identities described above.

The polypeptide compounds described herein can have amino acid residues which are modified without affecting biological activity. For example, the amino and carboxyl termini can be, and preferably are, derivatized. The amino terminal residue is preferably a pyroglutamate residue, although it can be a glutamate or glutamine residue if the compound will be delivered to a body location where an enzyme or group of enzymes that catalyzes conversion of a glutamate or glutamine residue to a pyroglutamate residue occurs. An enzyme that catalyzes this conversion, glutamyl cyclase, is widely distributed in mammalian tissues, including, for example, brain, pituitary, spleen, thymus, and kidney tissues. Thus, cyclization of an amino-terminal glutamate residue can be achieved in vitro (e.g., by contacting the polypeptide compound with a commercial preparation of a glutamyl cyclase in the presence of appropriate reagents) or in vivo (e.g., by delivering the polypeptide compound to a tissue in which a glutamyl cyclase occurs).

The carboxyl terminal residue should be blocked with a carboxyl terminus blocking moiety, preferably with an amine (—NH₂) moiety. Alternatively, the carboxyl terminus can be blocked by formation at the terminus of an ester, ketone, or higher amide moiety. Examples of suitable carboxyl terminus blocking ester and ketone moieties include methyl, ethyl, and propyl moieties, and examples of suitable carboxyl terminus blocking higher amide moieties include mono- and di-alkylamino groups such as methylamino, ethylamino, dimethylamino, diethylamino, methylethylamino moieties. Carboxyl terminal amidation can be achieved in vivo, for example by delivering the polypeptide compound to a cell or tissue in which enzymes that catalyze alpha-carboxyl amidation occur. By way of example, conversion of a polypeptide compound having a carboxyl terminal glycine residue to a polypeptide compound wherein the glycine residue is replaced by an (—NH₂) moiety (i.e., a carboxyl terminal amidated polypeptide compound) is catalyzed by the bi-functional enzyme designated peptidylglycine alpha-amidating monooxygenase (Prigge et al., 2000, Cell. Mol. Life Sci. 57(8–9):1236–1259). Thus, the carboxyl terminus of a polypeptide compound having a carboxyl terminal glycine residue can be achieved by delivering the compound to a cell or tissue in which that bi-functional enzyme is expressed. Reagents and methods for producing these carboxyl group derivatives in vitro are known in the art. By way of example, polypeptide compounds can be amidated in vitro using any of a number of known carboxypeptidase or transamidase enzymes (e.g., as described in Aasmul-Olsen et al., 1991, Biomed. Biochim. Acta 50(10–11):S106–S109; Merkler, 1994, Enzyme Microb. Technol. 16(6):450–456) or using the bi-functional peptidylglycine alpha-amidating monooxygenase. Chemical methods of amidating carboxyl acid residues are known, and substantially any of those methods can be used to amidate the carboxyl terminus of the polypeptide compounds described herein.

One or more of the naturally-occurring L-amino acid residues of the polypeptides described herein can be replaced with the corresponding D-isomeric form. Such residues can improve the stability of the compounds in vivo without significantly affecting their biological activity.

The polypeptide compounds can be provided in solution or as acid addition salts. Examples of suitable counter-ions include sodium, potassium, calcium, magnesium, ammonium, chloride, bromide, sulfate, nitrate, phosphate, acetate, propionate, butyrate, glycollate, pyruvate, oxalate, malate, malonate, succinate, maleate, fumarate, tartrate, citrate, benzoate, and other pharmaceutically acceptable counter-ions recognized in the art.

Compounds within the scope of formula I or formula III that are not explicitly disclosed herein can be screened using the methods described below (e.g., using the glycerol or palmitate release assays described in the Examples) to confirm that they exhibit lipid mobilizing activity in human cells (e.g., in human adipocytes). It is possible that one or more compounds within the scope of formulas I and III will exhibit little or no lipid mobilizing activity, and those compounds will have reduced or no use in the compositions and methods described herein.

The method by which the polypeptide compound is made or obtained is not critical. Polypeptide compounds that are useful in the compositions and methods described herein can be isolated from natural sources (e.g., from one or more of the insects listed in Table 1) or made synthetically or semi-synthetically.

A suitable method for purifying insect AKHs is described in Gäde et al. (1997, Biochem. J. 321:201–206). Of course, alternative methods can be used. In general, such methods comprise making an extract of insect cells, removing debris and relatively high (e.g., >2500, >3000, >5000, or >10000) molecular weight material and separating the remaining material using one or more chromatographic methods (e.g., traditional or high pressure chromatography using a reverse phase or gel filtration chromatographic column packing material). Fractions from a preparative step that contain the AKH can be identified by assaying activity (e.g., ability to promote lipid mobilization in human adipocytes) or using an immunological method (e.g., assaying the presence of a compound that cross-reacts with an antibody raised against a known AKH).

Traditional polypeptide synthetic methods can be used to make the polypeptide compounds described herein. The pyroglutamate residue at the amino terminus of the polypeptide compounds can be incorporated during synthesis or made by cyclizing an amino-terminal glutamate or glutamine residue following polypeptide synthesis (e.g., by contacting the polypeptide with a glutamate cyclase, optionally under alkaline conditions). Non-enzymatically-catalyzed cyclization of amino terminal glutamate residues occurs under alkaline conditions; pyroglutamate formation can be achieved by maintaining a polypeptide compound under alkaline conditions. The carboxyl-terminal amide moiety can be made by incorporating an alpha-carboxyl-amidated amino acid residue as the carboxyl terminal residue or by incorporating a normal (i.e., alpha-carboxyl) amino acid residue at the carboxyl terminus and thereafter amidating it. By way of example, traditional solid phase polypeptide synthetic methods using tert-butoxycarbonyl protecting groups, N-alpha-9-fluorenylmethoxycarbonyl protecting groups, or both, can be used to make the polypeptide compounds described herein.

Alternatively, the polypeptide compounds described herein can be obtained commercially. Numerous companies exist that will prepare polypeptide compounds to order, and any of those companies can be used as a source of the materials. At least some of the compounds are currently available from commercial sources. For example, Table 4 lists commercial sources for several AKHs described herein.

TABLE 4

| AKH | Company | Catalog Number | SEQ ID NO: |
| --- | --- | --- | --- |
| Migratory locust AKH I | American Peptide Co. (Sunnyvale, California) | 60-9-18 | 1 |
| Tropical cockroach hypertrehalosemic factor | Sigma Chemical Co. (St. Louis, Missouri) | P0175 | 2 |
| Desert locust AKH II | American Peptide Co. Peninsula Laboratories, Inc. (San Carlos, California) | 60-9-21 8864 | 4 |
| Corn ear worm, honey bee, and tobacco hornworm moth AKH I | Peninsula Laboratories, Inc. | 8882 | 3 |

The commercially available peptides listed in Table 4 have been tested and confirmed to exhibit lipid mobilizing activity in human and murine adipocytes. This information confirms that these four peptides (each of which has an amino-terminal pyroglutamate residue and an aminated carboxyl terminus) is suitable for use in the compositions and methods described herein.

Screening Methods

The insect AKH polypeptides described herein can be used to make antibody molecules (such as antibodies, single-chain antibodies, and antibody fragments comprising one or more antibody variable regions) that bind specifically with the polypeptide. Such antibodies can be used to purify the same AKH or polypeptides that share an epitope with the AKH from a suspension or solution. By way of example, an antibody that binds specifically with migratory locust AKH I can be used to isolate a polypeptide having a common epitope from a suspension prepared from a human, murine, bovine, porcine, or other mammalian cell or tissue sample. Other screening assays described herein can be used to assess whether the isolated polypeptide exhibits lipid mobilizing activity. In this way, AKHs from mammalian or other non-insect species can be isolated and identified.

Lipid mobilizing activity of a polypeptide (e.g., one of the AKHs described herein) can be assessed using any of a variety of assays for assessing lipolysis. For example, a glycerol release assay analogous to that described by Kitada et al., (1982, J. Cell. Biochem. 20(4):409–412) can be performed using lipid-containing cells, such as murine or human adipocytes. In a glycerol release assay, otherwise identical cells are separately incubated in the presence and absence of the polypeptide, and release of glycerol from the cells is assessed. Glycerol can be assayed using any of a variety of known procedures and commercial reagents (e.g., using a glycerol assay kit available from Sigma Chemical Company which is based on conversion of 2-(p-indophenyl)-3-p-nitrophenyl-5-phenyltetrazolium chloride to forman). Ability of a polypeptide to induce glycerol release from adipocytes is an indication that the polypeptide is an AKH, and relative degrees or rates of glycerol release among polypeptides can be used as a measure of the efficacy of the polypeptides as AKHs. Alternatively, cells can be incubated in the presence of a labeled lipid precursor (e.g., a radiolabeled carboxylic acid such as palmitate) in order to induce incorporation of the labeled precursor into lipids in the cells, and ability of a polypeptide to induce release of the label from the cells can be used as an indication of lipid mobilizing activity for the polypeptide. Thus, for example, release of label from labeled (e.g., radiolabeled) palmitate of human or murine adipocytes can be used to assess the efficacy of a polypeptide as an AKH.

Mobilization of Lipids in Human Cells

Lipids can be mobilized in a human cell (i.e., in vitro or in vivo) by administering to the cell one of the polypeptide compounds described herein. The compound can be an insect adipokinetic hormone, a polypeptide having the amino acid sequence of one of SEQ ID NOs: 1–40 wherein the amino-terminal glutamate residue is a pyroglutamate residue, a compound having a chemical structure according to formula I, or a compound having a chemical structure according to formula II. The compound can also be a derivative of one of these compounds, the derivative being made by a known peptide derivatization method and screened for adipokinetic activity as described herein. Alternatively, the compound can be a structural analog of one of these compounds, wherein the chemical structure of the analog is designed to mimic the chemical structure of one of the foregoing compounds and then screened for adipokinetic activity.

It is not critical whether the compound is administered directly to the cell, to a tissue comprising the cell, a body fluid that contacts the cell, or a body location from which the compound can diffuse or be transported to the cell. It is sufficient that the compound is administered to the human in an amount and by a route whereby an amount of the compound sufficient to mobilize lipids in the cell arrives, directly or indirectly at the cell. The minimum amount varies with the identity of the AKH, but is generally in the range from $10^{-9}$ to $10^{-5}$ molar, preferably in the range from $10^{-7}$ to $10^{-5}$ molar.

The cell to which the compound is provided (i.e., the "target cell") is not critical. However, because most cell types do not contain large lipid stores, the efficacy of the compound for mobilizing lipids in the human can be maximized by administering it to adipocytes or other cells know to contain significant lipid stores.

The polypeptide compound can be provided to the cell in vitro or in vivo. Alternatively, the compound can be provided to the cell outside the body prior to returning the cell to the body of the human from which it was obtained. When the compound is provided to a cell in vivo, the route of administration and the form in which the compound is administered are not critical, except that the compound should be administered to the cell in an amount effective to elicit mobilization of lipid in the cell. Lower limits of such amounts can be determined in vitro, and the form and route of administration for the compound can be adjusted to achieve at least the lowest effective concentration at the desired site of action.

Because insect AKHs can promote lipid mobilization in human cells, assessment of lipid mobilization in human cells in the presence of an insect AKH and in the presence of a test compound can indicate whether the test compound is able to enhance or inhibit lipid mobilization in the human cells. If lipid mobilization is greater in the presence of both the AKH and the test compound than it is in the presence of the AKH and the absence of the test compound, then this is an indication that the test compound is able to enhance lipid mobilization in humans (i.e., regardless of whether the test compound is administered to the human alone or together with an insect AKH). Similarly, if less or slower lipid mobilization occurs in the presence of both the AKH and the test compound than in the presence of the AKH and the absence of the test compound, then this is an indication that the test compound is able to inhibit lipid mobilization in humans. Using these methods, a skilled artisan can identify test compounds (e.g., antibodies or small molecules) that can be used to modulate lipid mobilization in humans. Such test compounds can be used to induce weight loss or weight gain by affecting lipid stores in a human to whom they are administered. These methods can also be used to identify antibodies that bind specifically with the human cell surface protein with which insect AKHs interact (i.e., an antibody that binds with the protein can inhibit or prevent interaction between the protein and the AKH), and those antibodies can be used to isolate and characterize the protein.

Other pharmaceutical agents (e.g., beta adrenergic agonists such as isoproterenol) are known to be able to induce or enhance mobilization of lipids in cells. Even though the mechanism(s) by which beta adrenergic agents enhance mobilization are not known with certainty, it is known that this activity can be inhibited by beta adrenergic receptor antagonists such as propanolol. The ability of the polypeptide compounds described herein to induce or enhance lipid mobilization is not significantly inhibited by propanolol, as the data described in the Examples demonstrate. This observation indicates that the polypeptide compounds described herein operate by a mechanism that is distinct (or at least different) from the mechanism associated with beta adrenergic agonist lipid mobilization. Consequences of the difference in the mechanisms for these types of compounds include i) that the polypeptide compounds described herein can be used in patients who, for any of a variety of reasons (e.g., hypersensitivity, immune reaction, or intolerable side effects) are unable to use beta adrenergic agonists for lipid mobilization; ii) that the polypeptide compounds can be effective in patients in whom beta adrenergic agonists have little or no efficacy for lipid mobilization; and iii) that the polypeptide compounds and beta adrenergic agonists can be used simultaneously (or in an overlapping fashion) in patients in order to yield cumulative or synergistic lipid mobilization.

Pharmaceutical Compositions

The form in which the polypeptide compound is administered to the cell is not critical; the compound need only reach the cell, directly or indirectly. The invention encompasses preparation and use of medicaments and pharmaceutical compositions comprising a polypeptide compound described herein (e.g., an insect AKH, a compound having the chemical structure of formula I or III, or a derivative or structural analog of one of these) as an active ingredient. The polypeptide compound is preferably highly purified prior to incorporating it into the pharmaceutical composition (e.g., purity of at least 75%, 80%, 90%, 95%, 98%, 99%, or nearly 100% pure, by weight of dry polypeptide in the purified sample).

A pharmaceutical composition can consist of the active ingredient alone, in a form (e.g., a salt) suitable for administration to a human, or the pharmaceutical composition can comprise the active ingredient and one or more pharmaceutically acceptable carriers, one or more additional ingredients, or some combination of these. Administration of one of these pharmaceutical compositions to a human is useful for mobilizing lipids, inhibiting or suppressing appetite, promoting weight loss in the human, or some combination of these purposes, as described elsewhere in the present disclosure. The active ingredient can be present in the pharmaceutical composition in the form of a physiologically acceptable ester or salt, such as in combination with a physiologically acceptable cation or anion, as is known in the art.

The formulations of the pharmaceutical compositions described herein can be prepared by any method known or hereafter developed in the art of pharmacology. In general, such preparatory methods include bringing the active ingredient into association with a carrier or one or more other accessory ingredients, and then, if necessary or desirable, shaping or packaging the product into a single- or multi-dose unit.

Although the descriptions of pharmaceutical compositions provided herein are principally directed to pharmaceutical compositions which are suitable for ethical administration to humans, it is understood that such compositions are generally suitable for administration to mammal of all sorts. Modification of pharmaceutical compositions suitable for administration to humans in order to render the compositions suitable for administration to various mammals is well understood, and the skilled veterinary pharmacologist can design and perform such modification with merely ordinary, if any, experimentation.

Pharmaceutical compositions that are useful in the methods of the invention can be prepared, packaged, or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a human or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the human treated and further depending upon the route by which the composition is to be administered. By way of example, the composition can comprise between 0.1% and 100% (w/w) active ingredient. A unit dose of a pharmaceutical composition of the invention will generally comprise from about 100 milligrams to about 2 grams of the active ingredient, and preferably comprises from about 200 milligrams to about 1.0 gram of the active ingredient.

In addition to the active ingredient, a pharmaceutical composition of the invention can further comprise one or more additional pharmaceutically active agents. Particularly contemplated additional agents include beta adrenergic receptor agonists (which can act synergistically with the polypeptide compounds described herein), serotonin re-uptake inhibitors (i.e., to reduce appetite), fat uptake blockers (to inhibit lipogenesis and fat deposition), and decoupling agents (e.g., thyroxine receptor binding agents).

Controlled- or sustained-release formulations of a pharmaceutical composition of the invention can be made using conventional technology.

A formulation of a pharmaceutical composition of the invention suitable for oral administration can be prepared, packaged, or sold in the form of a discrete solid dose unit including a tablet, a hard or soft capsule, a cachet, a troche, or a lozenge, each containing a predetermined amount of the active ingredient. Other formulations suitable for oral administration include a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture. Pharmaceutically acceptable excipients used in the manufacture of tablets include inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets can be non-coated or they can be coated using known methods to achieve delayed disintegration in the gastrointestinal tract of a human, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin.

Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Oral compositions can be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., 1987 Aliment. Pharmacol. Therap. 1:273–280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et al., 1984, J. Med. Chem. 27:261–268) and a variety of naturally available and modified polysaccharides (see PCT application PCT/GB89/00581) can be used in such formulations.

Pulsed release technology such as that described in U.S. Pat. No. 4,777,049 can also be used to administer the active agent to a specific location within the gastrointestinal tract. Such systems permit drug delivery at a predetermined time and can be used to deliver the active agent, optionally together with other additives that my alter the local microenvironment to promote agent stability and uptake, directly to the colon, without relying on external conditions other than the presence of water to provide in vivo release.

Liquid formulations of a pharmaceutical composition of the invention which are suitable for oral administration can be prepared, packaged, and sold either in liquid form or in the form of a dry product intended for reconstitution with water or another suitable vehicle prior to use.

Liquid suspensions can be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions can further comprise one or more additional ingredients including suspending agents, dispersing or wetting agents, emulsifying agents, demulcents, preservatives, buffers, salts, flavorings, coloring agents, and sweetening agents. Oily suspensions can further comprise a thickening agent. Known suspending agents include sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include lecithin and acacia. Known preservatives include methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents can be prepared in substantially the same manner as liquid suspensions, the primary difference being that the active ingredient is dissolved, rather than suspended in the solvent. Liquid solutions of the pharmaceutical composition of the invention can comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention can be prepared using known methods. Such formulations can be administered directly to a human, used, for example, to form tablets, to fill capsules, or to prepare an aqueous or oily suspension or solution by addition of an aqueous or oily vehicle thereto. Each of these formulations can further comprise one or more of dispersing or wetting agent, a suspending agent, and a preservative. Additional excipients, such as fillers and sweetening, flavoring, or coloring agents, can also be included in these formulations.

A pharmaceutical composition of the invention can also be prepared, packaged, or sold in the form of oil-in-water emulsion or a water-in-oil emulsion. The oily phase can be a vegetable oil such as olive or arachis oil, a mineral oil such as liquid paraffin, or a combination of these. Such compositions can further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions can also contain additional ingredients including, for example, sweetening or flavoring agents.

A pharmaceutical composition of the invention can be prepared, packaged, or sold in a formulation suitable for rectal administration. Such a composition can be in the form of, for example, a suppository, a retention enema preparation, and a solution for rectal or colonic irrigation.

Suppository formulations can be made by combining the active ingredient with a non-irritating pharmaceutically acceptable excipient which is solid at ordinary room temperature (i.e. about 20° C.) and which is liquid at the rectal temperature of the human (i.e. about 37° C. in a healthy human). Suitable pharmaceutically acceptable excipients include cocoa butter, polyethylene glycols, and various glycerides. Suppository formulations can further comprise various additional ingredients including antioxidants and preservatives.

Retention enema preparations or solutions for rectal or colonic irrigation can be made by combining the active ingredient with a pharmaceutically acceptable liquid carrier. As is known in the art, enema preparations can be administered using, and can be packaged within, a delivery device adapted to the rectal anatomy of a human. Enema preparations can further comprise various additional ingredients including antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Methods for impregnating or coating a material with a chemical composition are known in the art, and include methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation can be made by combining the active ingredient with a pharmaceutically acceptable liquid carrier. As is known in the art, douche preparations can be administered using, and can be packaged within, a delivery device adapted to the vaginal anatomy of a human. Douche preparations can further comprise various additional ingredients including antioxidants, antibiotics, antifungal agents, and preservatives.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations can be prepared, packaged, or sold in a form suitable for bolus administration or for continuous administration. Injectable formulations can be prepared, packaged, or sold in unit dosage form, such as in ampules, in multi-dose containers containing a preservative, or in single-use devices for auto-injection or injection by a medical practitioner. Formulations for parenteral administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butanediol, for example. Other acceptable diluents and solvents include Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

Formulations suitable for topical administration include liquid or semi-liquid preparations such as liniments, lotions, oil-in-water or water-in-oil emulsions such as creams, ointments or pastes, and solutions or suspensions. Topically-administrable formulations can, for example, comprise from about 0.1% to about 10% (w/w) active ingredient, although the concentration of the active ingredient can be as high as the solubility limit of the active ingredient in the solvent. Formulations for topical administration can further comprise one or more of the additional ingredients described herein.

A pharmaceutical composition of the invention can be prepared, packaged, or sold in a formulation suitable for pulmonary administration via the buccal cavity. Such a formulation can comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant can be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point below 65° F. at atmospheric pressure. Generally the propellant can constitute 50 to 99.9% (w/w) of the composition, and the active ingredient can constitute 0.1 to 20% (w/w) of the composition. The propellant can further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery can also provide the active ingredient in the form of droplets of a solution or suspension. Such formulations can be prepared, packaged, or sold as aqueous or dilute alcoholic solutions or suspensions, optionally sterile, comprising the active ingredient, and can conveniently be administered using any nebulization or atomization device. Such formulations can further comprise one or more additional ingredients including a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration can, for example, comprise from about as little as 0. 1% (w/w) and as much as 100% (w/w) of the active ingredient, and can further comprise one or more of the additional ingredients described herein.

A pharmaceutical composition of the invention can be prepared, packaged, or sold in a formulation suitable for buccal administration. Such formulations can, for example, be in the form of tablets or lozenges made using conventional methods, and can, for example, comprise 0.1 to 20% (w/w) active ingredient, the balance comprising an orally dissolvable or degradable composition and, optionally, one or more of the additional ingredients described herein. Alternately, formulations suitable for buccal administration can comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and can further comprise one or more of the additional ingredients described herein.

A pharmaceutical composition of the invention can be prepared, packaged, or sold in a formulation suitable for ophthalmic administration. Such formulations can, for example, be in the form of eye drops including, for example, a 0.1–1.0% (w/w) solution or suspension of the active ingredient in an aqueous or oily liquid carrier. Such drops can further comprise buffering agents, salts, or one or more other of the additional ingredients described herein. Other ophthalmalmically-administrable formulations which are useful include those which comprise the active ingredient in microcrystalline form or in a liposomal preparation.

A pharmaceutical composition can be prepared in the form of, or added to, a food (e.g., a processed item intended for direct consumption) or a foodstuff (e.g., an edible ingredient intended for incorporation into a food prior to ingestion). Examples of suitable foods include candies such as lollipops, baked goods such as crackers, breads, cookies, and snack cakes, whole, pureed, or mashed fruits and vegetables, beverages, and processed meat products. Examples of suitable foodstuffs include milled grains and sugars, spices and other seasonings, and syrups. The polypeptide compositions described herein are preferably not exposed to high cooking temperatures for extended periods of time, in order to minimize degradation of the compounds.

In one embodiment, a polypeptide compound is provided to a cell by providing to the cell a nucleic acid vector comprising a nucleic acid that encodes the polypeptide operably linked with a promoter/regulatory region. When the vector is provided to the cell, the polypeptide compound is made by the cell by way of expression of the nucleic acid and action of cellular enzymes on the resulting primary transcript (e.g., cyclization of the amino-terminal glutamate or glutamine residue. When the polypeptide compound by way of a nucleic acid vector, the vector encodes a polypeptide having the chemical structure of formula VI.

$$Xaa^0\text{-}Xaa^2\text{-}Xaa^3\text{-}Xaa^4\text{-}Xaa^5\text{-}Xaa^6\text{-}Xaa^7\text{-}Xaa^8\text{-}X \quad \text{(VI)}$$

In formula VI, $Xaa^0$ can be either a glutamate residue or a glutamine residue. Each of $Xaa^2$, $Xaa^3$, $Xaa^4$, $Xaa^5$, $Xaa^6$, $Xaa^7$, $Xaa^8$, and X have the identities described above. The nucleotide sequence used to encode the polypeptide of formula VI is not critical, although it can be preferable to use codons that are efficiently expressed in the cell (codon efficiency information being available in the art). Preferably, the encoded polypeptide has the amino acid sequence of one of SEQ ID NOs: 1–40. The promoter/regulatory region can be one that is specifically expressed only in cells of a certain type (e.g., adipocytes). Numerous cell type-specific and other selective promoter/regulatory regions are known.

As used herein, "additional ingredients" can include one or more of the following: excipients, surface active agents, dispersing agents, inert diluents, granulating and disintegrating agents, binding agents, lubricating agents, sweetening agents, flavoring agents, coloring agents, preservatives, physiologically degradable compositions such as gelatin, aqueous vehicles and solvents, oily vehicles and solvents, suspending agents, dispersing or wetting agents, emulsifying agents, demulcents, buffers, salts, thickening agents, fillers, emulsifying agents, antioxidants, antibiotics, antifungal agents, stabilizing agents, and pharmaceutically acceptable polymeric or hydrophobic materials. Other "additional ingredients" which can be included in the pharmaceutical compositions of the invention are known in the art and described, for example in Genaro, ed., 1985, Remington's Pharmaceutical Sciences, Mack Publishing Co., Easton, Pa., which is incorporated herein by reference.

A pharmaceutical composition of the invention can be administered to deliver a dose of between 1 nanogram per day per kilogram body weight and 100 milligrams per day per kilogram body weight, and preferably to deliver of between 100 milligrams and 2 grams, to a human.

It is understood that the ordinarily skilled physician or veterinarian will readily determine and prescribe an effective amount of the compound to mobilize lipid stores, induce weight loss, or inhibit appetite in the human. In so proceeding, the physician or veterinarian can, for example, prescribe a relatively low dose at first, subsequently increasing the dose until an appropriate response is obtained. It is further understood, however, that the specific dose level for any particular human will depend upon a variety of factors including the activity of the specific compound employed, the age, body weight, general health, gender, and diet of the human, the time of administration, the route of administration, the rate of excretion, any drug combination, and the severity of any disorder being treated.

Another aspect of the invention relates to a kit comprising a pharmaceutical composition of the invention and instructional material. Instructional material includes a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention also includes a kit comprising a pharmaceutical composition of the invention and a delivery device for delivering the composition to a human. By way of example, the delivery device can be a squeezable spray bottle, a metered-dose spray bottle, an aerosol spray device, an atomizer, a dry powder delivery device, a self-propelling solvent/powder-dispensing device, a syringe, a needle, a tampon, or a dosage measuring container. The kit can further comprise an instructional material as described herein.

EXAMPLES

The invention is now described with reference to the following Examples. These Examples are provided for the purpose of illustration only and the invention is not limited to these Examples, but rather encompasses all variations which are evident as a result of the teaching provided herein.

Example 1

Assessment of Lipid Mobilizing Activity for Selected Neuropeptides Using Labeled Palmitate In the experiments used in this Example, ability of selected insect AKHs to promote lipid mobilization in isolates of human adipocytes isolated at the time of liposuction was demonstrated.

Lipid mobilizing activity was assessed by assaying release of tritium label from radiolabeled palmitate. This assay was performed by maintaining human pre-adipocytes in Adipocyte Growth Medium (AGM), which is Dulbecco's Modified Eagle's Medium (DMEM) mixed 1:1 by volume with Ham's F-10 medium. Ham's F-10 medium comprises 15 millimolar HEPES buffer adjusted to pH 7.4 and supplemented with biotin, pantothenate, human recombinant insulin, dexamethasone, fungicide, bactericide, and 3% (v/v) fetal bovine serum). Pre-adipocytes differentiated to become mature adipocytes by three weeks of maintenance in AGM. On the day prior to assay, the adipocytes were washed and incubated overnight in Krebs-Ringers buffer comprising 0.1% fatty acid-free bovine serum albumin (BSA) and comprising 1 microCurie per milliliter of tritiated (9,10-$^3$H) palmitate. The following day, the medium was removed, and the cells were washed three times in. Isoproterenol (0 to $5\times10^{-8}$ molar), Schistocera gregaria AKH II (0 to $5\times10^{-5}$ molar), or Krebs-Ringer buffer (with 0.1% fatty acid-free BSA) containing neither of these was added to the cell suspension in a volume of 150 microliters. The suspensions were incubated for 4 hours at 37° C., and then 100 microliters of each sample was subjected to scintillation counting to detect released label in the supernatant. The total amount of label incorporated was determined for each well by solubilizing the cells using 1% sodium dodecyl sulfate and subjecting the entire contents of the well to scintillation counting. Fractional release of label was calculated by dividing the amount of label detected in cell supernatant by the total amount of label detected in the supernatant and in the cells remaining in the well, and percentage release was calculated by multiplying fractional release by 100. Percentage release of label is indicated in Table 5.

TABLE 5

| Concentration of Agent | % Tritium Label Release with Agent | |
|---|---|---|
| | Isoproterenol | S. g. AKHII |
| 0 | 9.08 | 11.8 |
| $5 \times 10^{-12}$ | 10.12 | |
| $1 \times 10^{-11}$ | 9.9 | |
| $5 \times 10^{-11}$ | 10.62 | |
| $1 \times 10^{-10}$ | 11.11 | 10.74 |
| $5 \times 10^{-10}$ | 11.21 | |
| $1 \times 10^{-9}$ | 12.67 | 9.6 |
| $5 \times 10^{-9}$ | 14.14 | |
| $1 \times 10^{-8}$ | 15.58 | 10.76 |
| $5 \times 10^{-8}$ | 16.99 | |
| $1 \times 10^{-7}$ | | 10.76 |
| $5 \times 10^{-7}$ | | 11.31 |
| $1 \times 10^{-6}$ | | 13.38 |
| $5 \times 10^{-6}$ | | 14.94 |
| $1 \times 10^{-5}$ | | 14.28 |
| $5 \times 10^{-5}$ | | 16.65 |

A similar study was done using the same methods, except that cockroach hypertrehalosemic factor (0 to $5\times10^{-5}$ molar) was used in place of S. gregaria AKH II. The results of this experiment are listed in Table 6.

TABLE 6

| Concentration of Agent | % Tritium Label Release with Agent | |
|---|---|---|
| | Isoproterenol | Cr. HTP |
| 0 | 8.16 | 8.03 |
| $5 \times 10^{-12}$ | 6.81 | |
| $1 \times 10^{-11}$ | 5.87 | |
| $5 \times 10^{-11}$ | 6.96 | |
| $1 \times 10^{-10}$ | 8.97 | 7.21 |
| $5 \times 10^{-10}$ | 7.58 | |
| $1 \times 10^{-9}$ | 6.67 | 6.88 |
| $5 \times 10^{-9}$ | 5.93 | |
| $1 \times 10^{-8}$ | 9.8 | 7.24 |
| $5 \times 10^{-8}$ | 10.8 | |
| $1 \times 10^{-7}$ | | 7.17 |
| $5 \times 10^{-7}$ | | 8.08 |
| $1 \times 10^{-6}$ | | 8.77 |
| $5 \times 10^{-6}$ | | 9.36 |
| $1 \times 10^{-5}$ | | 9.08 |
| $5 \times 10^{-5}$ | | 9.7 |

A similar tritium label release experiment performed using Heliothis zea AKH II and Locusta migratoria, except that a two-hour incubation period was used in place of a 4 hour incubation period. The results of this experiment are listed in Table 7.

TABLE 7

| Concentration of Agent (molar) | % Tritium Label Release with Agent | |
|---|---|---|
| | Heliothis AKH II | Locusta AKH I |
| 0 | 6.04 | 6.04 |
| $1 \times 10^{-10}$ | 5.79 | 7.62 |
| $1 \times 10^{-9}$ | 5.52 | 7.44 |
| $1 \times 10^{-8}$ | 5.12 | 7.00 |
| $1 \times 10^{-7}$ | 5.72 | 6.34 |
| $1 \times 10^{-6}$ | 5.77 | 7.52 |
| $1 \times 10^{-5}$ | 10.5 | 10.8 |

These results demonstrate that each of Schistocera gregaria AKH II, cockroach hypertrehalosemic factor, Heliothis zea AKH II, and Locusta migratoria AKH I is able to mobilize lipids in murine adipocytes, and therefore in humans. Minimum effective concentrations of these agents appear to be about $10^6$ molar for Schistocera gregaria AKH II and about $5\times10^7$ molar for cockroach hypertrehalosemic factor in the conditions used in these experiments.

Example 2

Glycerol Release Assessment of Lipid Mobilizing Activity for Selected Neuropeptides In the experiments used in this Example, ability of selected insect AKHs to promote lipid mobilization in human adipocytes was demonstrated by assessing glycerol release from the adipocytes in the presence of selected concentrations of the AKHs.

Human pre-adipocytes were isolated by liposuction and maintained in AGM for three weeks in order to permit the pre-adipocytes to differentiate to become mature adipocytes. AGM was removed, and adipocytes were incubated in Krebs-Ringers buffer comprising 0.1% fatty acid-free BSA at 37° C. for five hours in the presence of selected concentrations ($10^{-9}$ to $10^{-5}$ molar) of one of Schistocera gregaria AKH II, cockroach hypertrehalosemic factor (obtained from Sigma Chemical Co, St. Louis, Mo., catalog number P0175), and *Locusta migratoria* AKH I (obtained from American Peptide Co., Sunnyvale, Calif., catalog number 60-9-18). Glycerol released from the adipocytes was assayed using a commercially available kit (GPO-trinder assay kit available form Sigma Chemical Company, St. Louis, Mo.). Glycerol release in the presence of each of these agents is shown in Table 8.

TABLE 8

| Concentration of Agent | Glycerol Release with Agent (medium concentration in millimolar) | | |
|---|---|---|---|
| | Schistocera | Locusta | Cockroach |
| 0 | 0.438 | 0.438 | 0.438 |
| $1 \times 10^{-9}$ | 0.486 | 0.611 | 0.603 |
| $1 \times 10^{-8}$ | 0.523 | 0.476 | 0.451 |
| $1 \times 10^{-7}$ | 0.530 | 0.490 | 0.527 |
| $1 \times 10^{-6}$ | 0.628 | 0.467 | 0.555 |
| $1 \times 10^{-5}$ | 0.693 | 0.691 | 1.124 |

A similar experiment was performed, in which glycerol release from adipocytes was assessed in the presence of the *Locusta migratoria* AKH I or the cockroach hypertrehalosemic factor or in the presence of isoproterenol. Glycerol release in the presence of each of these agents is shown in Table 9.

TABLE 9

| Concentration of Agent | Glycerol Release with Agent (medium concentration in millimolar) | | |
|---|---|---|---|
| | Isoproterenol | Locusta | Cockroach |
| $1 \times 10^{-9}$ | 0.0381 ± 0.011 | | |
| $1 \times 10^{-8}$ | 0.1325 ± 0.0244 | 0.0209 ± 0.0110 | 0.0817 ± 0.0113 |
| $1 \times 10^{-7}$ | 0.2169 ± 0.0316 | 0.0336 ± 0.0082 | 0.0944 ± 0.00166 |
| $1 \times 10^{-6}$ | 0.5172 ± 0.1659 | 0.0427 ± 0.0129 | 0.1216 ± 0.0103 |
| $1 \times 10^{-5}$ | | 0.0871 ± 0.0134 | 0.1515 ± 0.0155 |

These results demonstrate that the insect AKHs *Schistocera gregaria* AKH II, cockroach hypertrehalosemic factor, and *Locusta migratoria* AKH I are able to promote lipid mobilization in human adipocytes. In both tritium label release assays and glycerol release assays, the AKH-promoted activity was far less affected by the presence of propanolol than was isoproterenol-promoted lipid mobilizing activity. This observation suggests that AKH-promoted lipid mobilization occurs by a mechanism that is at least partly distinct from the mechanism of action of isoproterenol.

No lipid mobilizing activity could be detected for alpha-melanocyte stimulating hormone (which has the amino acid sequence SYSMEHFRWGKPV {SEQ ID NO: 41}, wherein the amino-terminal serine is acetylated and the carboxyl-terminal valine residue is aminated), melanocyte concentrating hormone (which has the amino acid sequence DFDMLRCMLGRVYRPCWQV {SEQ ID NO: 42}, wherein the two cysteine residues are linked by a disulfide linkage), or anorexigenic hormone (which has the amino acid sequence EHG, wherein the amino-terminal glutamate residue is a pyroglutamate residue).

Example 3

Effect of Propanolol on AKH-Induced Glycerol Release

Glycerol release assays were performed as described in Example 2, except that the assays were performed using single selected concentrations of one of cockroach hypertrehalosemic factor, *Locusta migratoria* AKH I, and isoproterenol and multiple selected concentrations of propanolol. Glycerol release in the presence of each of these agents is shown in Table 10.

TABLE 10

| Concentration of Propanolol (molar) | Glycerol Release with Agent (medium concentration in millimolar) | | | |
|---|---|---|---|---|
| | No Agent | Isoproterenol (1 micromolar) | Locusta (10 micromolar) | Cockroach (10 micromolar) |
| 0 | | 0.5172 | 0.0871 ± 0.0134 | 0.1515 ± 0.0155 |
| $1 \times 10^{-8}$ | 0.0399 ± 0.0083 | | | |
| $1 \times 10^{-7}$ | 0.0399 ± 0.0069 | 0.6533 | 0.2486 ± 0.0249 | 0.1161 ± 0.0232 |
| $1 \times 10^{-6}$ | 0.0417 ± .00072 | 0.411 | 0.2169 ± 0.0294 | 0.1370 ± 0.0170 |
| $1 \times 10^{-5}$ | 0.0463 ± 0.0042 | 0.2305 | 0.2214 ± 0.0287 | 0.2033 ± 0.0134 |

The results disclosed in this Example confirm (as was previously known) that propanolol is able to inhibit glycerol release from adipocytes induced by isoproterenol. The results also demonstrate that propanolol does not significantly inhibit glycerol release from adipocytes induced by either of the two insect AKHs that were tested. These observations indicate that insect AKHs are able to mobilize lipids in adipocytes by a mechanism different from the mechanism by which isoproterenol exerts its action. These results suggest that insect AKHs and isoproterenol (or other beta adrenergic agonists) can be used complementarily or synergistically to mobilize lipids in human adipocytes.

The disclosure of every patent, patent application, and publication cited herein is hereby incorporated herein by reference in its entirety.

Although this invention has been disclosed with reference to specific embodiments, it is apparent that other embodiments and variations of this invention can be devised by others skilled in the art without departing from the true spirit and scope of the invention. The invention, as set forth in the appended claims, includes all such embodiments and equivalent variations.

We claim:

1. A method of promoting lipid mobilization in a human, the method comprising administering an insect adipokinetic hormone to the human in an amount effective to mobilize lipids in the human.

2. The method of claim 1, wherein the hormone has a molecular weight less than 2500.

3. The method of claim 1, wherein the hormone is a polypeptide having a pyroglutamate residue at its amino terminus.

4. The method of claim 1, wherein the hormone is a polypeptide having a blocked carboxyl terminus.

5. The method of claim 4, wherein the carboxyl terminus of the polypeptide is amidated.

6. The method of claim 1, wherein the hormone is a polypeptide that does not have internal disulfide bonds.

7. The method of claim 1, wherein the hormone is characterized in that its ability to promote lipid mobilization is not significantly inhibited by propanolol.

8. The method of claim 1, wherein the hormone is a polypeptide characterized in that:
   i) it has a molecular weight less than 2500;
   ii) it has a pyroglutamate residue at its amino terminus;
   iii) it is amidated at its carboxyl terminus;
   iv) it does not have internal disulfide bonds; and
   v) its ability to promote lipid mobilization is not significantly inhibited by propanolol.

9. The method of claim 1, wherein the hormone has the chemical structure $$Xaa^1\text{-}Xaa^2\text{-}Xaa^3\text{-}Xaa^4\text{-}Xaa^5\text{-}Xaa^6\text{-}Xaa^7\text{-}Xaa^8\text{-}X\text{-}Z,$$

wherein:
   $Xaa^1$ is a pyroglutamate residue;
   $Xaa^2$ is one of a leucine residue, an isoleucine residue, a valine residue, a phenylalanine residue, and a tyrosine residue;
   $Xaa^3$ is one of an asparagine residue and a threonine residue;
   $Xaa^4$ is one of a phenylalanine residue and a tyrosine residue;
   $Xaa^5$ is one of a threonine residue and a serine residue;
   $Xaa^6$ is one of a proline residue, a serine residue, a threonine residue, and an alanine residue;
   $Xaa^7$ is one of a glycine residue, an asparagine residue, a serine residue, an aspartate residue, a valine residue, and a tryptophan residue;
   $Xaa^8$ is a tryptophan residue;
   X is from 0 to 10 amino acid residues; and
   Z is one of a hydrogen radical and a carboxyl terminus-blocking moiety.

10. The method of claim 9, wherein:
   $Xaa^2$ is one of a leucine residue and a valine residue;
   $Xaa^6$ is one of a proline residue, a serine residue, and a threonine residue;
   $Xaa^7$ is one of a glycine residue, an asparagine residue, and a serine residue;
   $Xaa^8$ is a tryptophan residue;
   X is from 0 to 3 amino acid residues; and
   Z is an ($-NH_2$) radical.

11. The method of claim 10, wherein $Xaa^4$ is a phenylalanine residue.

12. The method of claim 9, wherein:
   X is 0 amino acid residues; and
   Z is an ($-NH_2$) radical.

13. The method of claim 9, wherein X is a glycine residue.

14. The method of claim 13, wherein Z is an ($-NH_2$) radical.

15. The method of claim 9, wherein X has the chemical structure $$Xaa^9\text{-}Xaa^{10}$$

wherein:
   $Xaa^9$ is a glycine residue; and
   $Xaa^{10}$ is one of a threonine residue, a glycine residue, a tryptophan residue, a serine residue, and an asparagine residue.

16. The method of claim 15, wherein $Xaa^{10}$ a threonine residue.

17. The method of claim 15, wherein Z is an ($-NH_2$) radical.

18. The method of claim 9, wherein X has the chemical structure $$Xaa^9\text{-}Xaa^{10}\text{-}Xaa^{11}$$

wherein:
   $Xaa^9$ is a glycine residue;
   $Xaa^{10}$ is one of a threonine residue, a glycine residue, a tryptophan residue, a serine residue, and an asparagine residue; and
   $Xaa^{11}$ is a lysine residue.

19. The method of claim 9, wherein X has the chemical structure $$Xaa^9\text{-}Xaa^{10}\text{-}Xaa^{11}\text{-}(Xaa^{12})_n$$

wherein
   n is from 0 to 7
   $Xaa^9$ is a glycine residue,
   $Xaa^{10}$, when present, is one of a threonine residue, a glycine residue, a tryptophan residue, a serine residue, and an asparagine residue;
   $Xaa^{11}$, when present, is a lysine residue; and
   each $Xaa^{12}$, when present, is any amino acid residue.

20. The method of claim 9, wherein X is a glycine residue and Z is a hydrogen radical.

21. The method of claim 9, wherein the hormone is administered in an amount in the range from 100 milligrams to about 2 grams per day.

22. The method of claim 21, wherein the hormone is administered in an amount in the range from 200 milligrams to 1.0 gram per day.

23. The method of claim 1, wherein the hormone has the chemical structure $$Xaa^1\text{-}Xaa^{22}\text{-}Xaa^{23}\text{-}Xaa^{24}\text{-}Xaa^{25}\text{-}Xaa^{26}\text{-}Xaa^{27}\text{-}Xaa^{28}\text{-}X\text{-}Z,$$

wherein:
   $Xaa^1$ is a pyroglutamate residue;
   $Xaa^{22}$ is an amino acid residue having a non-polar side chain;
   $Xaa^{23}$ is an amino acid residue having a non-ionic polar side chain;
   $Xaa^{24}$ is an amino acid residue having an aromatic side chain;
   $Xaa^{25}$ is an amino acid residue having a non-ionic polar side chain;
   $Xaa^{26}$ is any amino acid residue;
   $Xaa^{27}$ is any amino acid residue;
   $Xaa^{28}$ is an amino acid residue having an aromatic side chain;
   X is from 0 to 10 amino acid residues; and
   Z is one of a hydrogen radical and a carboxyl terminus-blocking moiety.

24. The method of claim 23, wherein:
   $Xaa^{26}$ is one of a proline residue, a serine residue, a threonine residue, and an alanine residue.

25. The method of claim 23, wherein:
   $Xaa^{27}$ is one of a glycine residue, an asparagine residue, a serine residue, a glutamate residue, a valine residue, and a tryptophan residue.

26. The method of claim 23, wherein Z is an ($-NH_2$) radical.

27. The method of claim 26, wherein X is 0 amino acid residues.

28. The method of claim 23, wherein X is a glycine residue and Z is a hydrogen radical.

29. A method of promoting lipid mobilization in a human, the method comprising administering to the human, in an amount effective to mobilize lipids in the human, a compound having the chemical structure $Xaa^1\text{-}Xaa^2\text{-}Xaa^3\text{-}Xaa^4\text{-}Xaa^5\text{-}Xaa^6\text{-}Xaa^7\text{-}Xaa^8\text{-}X\text{-}Z,$ wherein:
$Xaa^1$ is a pyroglutamate residue;
$Xaa^2$ is one of a leucine residue, an isoleucine residue, a valine residue, a phenylalanine residue, and a tyrosine residue;
$Xaa^3$ is one of an asparagine residue and a threonine residue;
$Xaa^4$ is one of a phenylalanine residue and a tyrosine residue;
$Xaa^5$ is one of a threonine residue and a seine residue;
$Xaa^6$ is one of a proline residue, a serine residue, a threonine residue, and an alanine residue;
$Xaa^7$ is one of a glycine residue, an asparagine residue, a seine residue, an aspartate residue, a valine residue, and a tryptophan residue;
$Xaa^8$ is a tryptophan residue;
X is from 0 to 10 amino acid residues; and
Z is one of a hydrogen radical and a carboxyl terminus-blocking moiety.

30. A method of promoting lipid mobilization in a human, the method comprising administering to the human, in an amount effective to mobilize lipids in the human, a compound having the chemical structure $Xaa^1\text{-}Xaa^{22}\text{-}Xaa^{23}\text{-}Xaa^{24}\text{-}Xaa^{25}\text{-}Xaa^{26}\text{-}Xaa^{27}\text{-}Xaa^{28}\text{-}X\text{-}Z,$ wherein:
$Xaa^1$ is a pyroglutamate residue;
$Xaa^{22}$ is an amino acid residue having a non-polar side chain;
$Xaa^{23}$ is an amino acid residue having a non-ionic polar side chain;
$Xaa^{24}$ is an amino acid residue having an aromatic side chain;
$Xaa^{25}$ is an amino acid residue having a non-ionic polar side chain;
$Xaa^{26}$ is any amino acid residue;
$Xaa^{27}$ is any amino acid residue;
$Xaa^{28}$ is an amino acid residue having an aromatic side chain;
X is from 0 to 10 amino acid residues; and
Z is one of a hydrogen radical and a carboxyl terminus-blocking moiety.

31. A method of promoting weight loss in a human, the method comprising administering an insect adipokinetic hormone to the human in an amount effective to mobilize lipids in the human.

32. The method of claim 11, wherein the human is afflicted with obesity.

33. A method of suppressing the appetite of a human, the method comprising administering an insect adipokinetic hormone to the human in an amount effective to mobilize lipids in the human, whereby the human's appetite is suppressed.

34. A method of promoting lipid mobilization in a human, the method comprising administering an insect adipokinetic hormone to the human in an amount effective to mobilize lipids in the human, wherein the hormone has the chemical structure $Xaa^1\text{-}Xaa^3\text{-}Xaa^4\text{-}Xaa^5\text{-}Xaa^6\text{-}Xaa^7\text{-}Xaa^8\text{-}Z,$ wherein:
$Xaa^1$ is a pyroglutamate residue;
$Xaa^3$ is one of an asparagine residue and a threonine residue;
$Xaa^4$ is one of a phenylalanine residue and a tyrosine residue;
$Xaa^5$ is one of a threonine residue and a serine residue;
$Xaa^6$ is one of a proline residue, a serine residue, a threonine residue, and an alanine residue;
$Xaa^7$ is one of a glycine residue, an asparagine residue, a serine residue, an aspartate residue, a valine residue, and a tryptophan residue;
$Xaa^8$ is a tryptophan residue; and
Z is one of a hydrogen radical and a carboxyl terminus-blocking moiety.

35. A method of promoting lipid mobilization in a human, the method comprising administering an insect adipokinetic hormone to the human in an amount effective to mobilize lipids in the human, wherein the hormone has the chemical structure $Xaa^1\text{-}Xaa^3\text{-}Xaa^4\text{-}Xaa^5\text{-}Xaa^6\text{-}Lys\text{-}Z,$ wherein:
$Xaa^1$ is a pyroglutamate residue;
$Xaa^3$ is one of an asparagine residue and a threonine residue;
$Xaa^4$ is one of a phenylalanine residue and a tyrosine residue;
$Xaa^5$ is one of a threonine residue and a seine residue;
$Xaa^6$ is one of a proline residue, a serine residue, a threonine residue, and an alanine residue; and
Z is one of a hydrogen radical and a carboxyl terminus-blocking moiety.

36. The method of claim 1, wherein the hormone is a polypeptide having the amino acid sequence SEQ ID NO: 4.

37. The method of claim 31, wherein the hormone is a polypeptide having the amino acid sequence SEQ ID NO: 4.

38. The method of claim 29, wherein the compound is a polypeptide having the amino acid sequence SEQ ID NO: 4.

39. The method of claim 30, wherein the compound is a polypeptide having the amino acid sequence SEQ ID NO: 4.

40. The method of claim 1, wherein the hormone is an adipokinetic hormone of an insect selected from the group consisting of locusts, bees, dragonflies, flies, butterflies, tobacco hornworm moths, beetles, grasshoppers, crickets, cockroaches, mantids, periodical cicadas, stick insects, firebugs, and corn ear worms.

41. The method of claim 1, wherein the hormone is an adipokinetic hormone of an insect selected from the group consisting of desert locusts, migratory locusts, honey bees, emperor dragonflies, damselflies, sawflies, fruit flies, horse flies, tenebrionid beetles, dung beetles, african pyrgomorphid grasshoppers, king crickets, ground crickets, american cockroaches, tropical cockroaches, and primitive cockroaches.

42. The method of claim 1, wherein the hormone is an adipokinetic hormone of an insect selected from the group consisting of *Schistocera gregaria, Locusts migratoria, Apis* mellifera, Libellula auripennis, Anax imperator, Pseudagrion inconspicuum, Ishnura senegalensis, Tenthredo arcuata, Drosophila melanogaster, Tabanus atratus, Phormia terraenova, Vanessa cardui, Manduca sexta, Melolontha melolontha, Geotrupes stercorosus, Tenebrio molitor, Zophobas rugipes, Phymateus leprosus, Melanoplus sanguinipes, Dictyophorus spumans, Phymateus morbillosus, Gryllodes sigillatus, Libanasidus vittatus, Heterodes namaqua, Acanthoproctus cervinus, Periplaneta americana, Leucophaea maderae, Gromphadorhina portenetosa, Blattella germanica, Blaberus discoidalis, Polyphaga aegyptiaca, Empusa pennata, Platypleura capensis, Cacama valavata, Diceroprocta semicinta, Extatosoma tiaratum, Pyrrhocoris apterus, and Heliothis zea.

43. The method of claim 1, wherein the hormone is an adipokinetic hormone of an insect selected from the group consisting of desert locusts, migratory locusts, honey bees, tobacco hornworm moths, grasshoppers, cockroaches, and corn ear worms.

44. The method of claim 1, wherein the hormone is an adipokinetic hormone of an insect selected from the group consisting of Schistocera gregaria, Locusta migratoria, Apis mellifera, Manduca sexta, Melanoplus sanguinipes, Gromphadorhina portenetosa, Blattella germanica, Blaberus discoidalis, and Heliothis zea.

45. The method of claim 31, wherein the hormone is an adipokinetic hormone of an insect selected from the group consisting of locusts, bees, dragonflies, flies, butterflies, tobacco hornworm moths, beetles, grasshoppers, crickets, cockroaches, mantids, periodical cicadas, stick insects, firebugs, and corn ear worms.

46. The method of claim 31, wherein the hormone is an adipokinetic hormone of an insect selected from the group consisting of desert locusts, migratory locusts, honey bees, emperor dragonflies, damselflies, sawflies, fruit flies, horse flies, tenebrionid beetles, dung beetles, african pyrgomorphid grasshoppers, king crickets, ground crickets, american cockroaches, tropical cockroaches, and primitive cockroaches.

47. The method of claim 31, wherein the hormone is an adipokinetic hormone of an insect selected from the group consisting of Schistocera gregaria, Locusta migratoria, Apis mellifera, Libellula auripennis, Anax imperator, Pseudagrion inconspicuum, Ishnura senegalensis, Tenthredo arcuata, Drosophila melanogaster, Tabanus atratus, Phormia terraenova, Vanessa cardui, Manduca sexta, Melolontha melolontha, Geotrupes stercorosus, Tenebrio molitor, Zophobas rugipes, Phymateus leprosus, Melanoplus sanguinipes, Dictyophorus spumans, Phymateus morbillosus, Gryllodes sigillatus, Libanasidus vittatus, Heterodes namaqua, Acanthoproctus cervinus, Periplaneta americana, Leucophaea maderae, Gromphadorhina portenetosa, Blattella germanica, Blaberus discoidalis, Polyphaga aegyptiaca, Empusa pennata, Platypleura capensis, Cacama valavata, Diceroprocta semicinta, Extatosoma tiaratum, Pyrrhocoris apterus, and Heliothis zea.

48. The method of claim 31, wherein the hormone is an adipokinetic hormone of an insect selected from the group consisting of desert locusts, migratory locusts, honey bees, tobacco hornworm moths, grasshoppers, cockroaches, and corn ear worms.

49. The method of claim 31, wherein the hormone is an adipokinetic hormone of an insect selected from the group consisting of Schistocera gregaria, Locusta migratoria, Apis mellifera, Manduca sexta, Melanoplus sanguinipes, Gromphadorhina portenetosa, Blattella germanica, Blaberus discoidalis, and Heliothis zea.

50. The method of claim 33, wherein the hormone is an adipokinetic hormone of an insect selected from the group consisting of locusts, bees, dragonflies, flies, butterflies, tobacco hornworm moths, beetles, grasshoppers, crickets, cockroaches, mantids, periodical cicadas, stick insects, firebugs, and corn ear worms.

51. The method of claim 33, wherein the hormone is an adipokinetic hormone of an insect selected from the group consisting of desert locusts, migratory locusts, honey bees, emperor dragonflies, damselflies, sawflies, fruit flies, horse flies, tenebrionid beetles, dung beetles, african pyrgomorphid grasshoppers, king crickets, ground crickets, american cockroaches, tropical cockroaches, and primitive cockroaches.

52. The method of claim 33, wherein the hormone is an adipokinetic hormone of an insect selected from the group consisting of Schistocera gregaria, Locusta migratoria, Apis mellifera, Libellula auripennis, Anax imperator, Pseudagrion inconspicuum, Ishnura senegalensis, Tenthredo arcuata, Drosophila melanogaster, Tabanus atratus, Phormia terraenova, Vanessa cardui, Manduca sexta, Melolontha melolontha, Geotrupes stercorosus, Tenebrio molitor, Zophobas rugipes, Phymateus leprosus, Melanoplus sanguinipes, Dictyophorus spumans, Phymateus morbillosus, Gryllodes sigillatus, Libanasidus vittatus, Heterodes namaqua, Acanthoproctus cervinus, Periplaneta americana, Leucophaea maderae, Gromphadorhina portenetosa, Blattella germanica, Blaberus discoidalis, Polyphaga aegyptiaca, Empusa pennata, Platypleura capensis, Cacama valavata, Diceroprocta semicinta, Extatosoma tiaratum, Pyrrhocoris apterus, and Heliothis zea.

53. The method of claim 33, wherein the hormone is an adipokinetic hormone of an insect selected from the group consisting of desert locusts, migratory locusts, honey bees, tobacco hornworm moths, grasshoppers, cockroaches, and corn ear worms.

54. The method of claim 33, wherein the hormone is an adipokinetic hormone of an insect selected from the group consisting of Schistocera gregaria, Locusta migratoria, Apis mellifera, Manduca sexta, Melanoplus sanguinipes, Gromphadorhina portenetosa, Blattella germanica, Blaberus discoidalis, and Heliothis zea.

* * * * *

SEQUENCE LISTING

<160> NUMBER OF SEQ ID NOS: 42

<210> SEQ ID NO 1
<211> LENGTH: 10

```
<212> TYPE: PRT
<213> ORGANISM: Schistocerca gregaria

<400> SEQUENCE: 1

Glu Leu Asn Phe Thr Pro Asn Trp Gly Thr
1               5                   10

<210> SEQ ID NO 2
<211> LENGTH: 10
<212> TYPE: PRT
<213> ORGANISM: Gromphadorhina portentosa

<400> SEQUENCE: 2

Glu Val Asn Phe Ser Pro Gly Trp Gly Thr
1               5                   10

<210> SEQ ID NO 3
<211> LENGTH: 9
<212> TYPE: PRT
<213> ORGANISM: Apis mellifera

<400> SEQUENCE: 3

Glu Leu Thr Phe Thr Ser Ser Trp Gly
1               5

<210> SEQ ID NO 4
<211> LENGTH: 8
<212> TYPE: PRT
<213> ORGANISM: Schistocerca gregaria

<400> SEQUENCE: 4

Glu Leu Asn Phe Ser Thr Gly Trp
1               5

<210> SEQ ID NO 5
<211> LENGTH: 8
<212> TYPE: PRT
<213> ORGANISM: Pseudagrion inconspicuum

<400> SEQUENCE: 5

Glu Val Asn Phe Thr Pro Gly Trp
1               5

<210> SEQ ID NO 6
<211> LENGTH: 8
<212> TYPE: PRT
<213> ORGANISM: Drosophila melanogaster

<400> SEQUENCE: 6

Glu Leu Thr Phe Ser Pro Asp Trp
1               5

<210> SEQ ID NO 7
<211> LENGTH: 8
<212> TYPE: PRT
<213> ORGANISM: Phormia terraenova

<400> SEQUENCE: 7

Glu Leu Thr Phe Ser Pro Asp Trp
1               5

<210> SEQ ID NO 8
<211> LENGTH: 9
<212> TYPE: PRT
<213> ORGANISM: Vanessa cardui
```

-continued

```
<400> SEQUENCE: 8

Glu Leu Thr Phe Thr Ser Ser Trp Gly
1               5

<210> SEQ ID NO 9
<211> LENGTH: 8
<212> TYPE: PRT
<213> ORGANISM: Pyrrhocoris apterus

<400> SEQUENCE: 9

Glu Leu Asn Phe Thr Pro Asn Trp
1               5

<210> SEQ ID NO 10
<211> LENGTH: 8
<212> TYPE: PRT
<213> ORGANISM: Locusta migratoria

<400> SEQUENCE: 10

Glu Leu Asn Phe Thr Pro Trp Trp
1               5

<210> SEQ ID NO 11
<211> LENGTH: 8
<212> TYPE: PRT
<213> ORGANISM: Locusta migratoria

<400> SEQUENCE: 11

Glu Leu Asn Phe Ser Ala Gly Trp
1               5

<210> SEQ ID NO 12
<211> LENGTH: 8
<212> TYPE: PRT
<213> ORGANISM: Periplaneta americana

<400> SEQUENCE: 12

Glu Val Asn Phe Ser Pro Asn Trp
1               5

<210> SEQ ID NO 13
<211> LENGTH: 8
<212> TYPE: PRT
<213> ORGANISM: Melolontha melolontha

<400> SEQUENCE: 13

Glu Leu Asn Tyr Ser Pro Asp Trp
1               5

<210> SEQ ID NO 14
<211> LENGTH: 8
<212> TYPE: PRT
<213> ORGANISM: Tabanus atratus

<400> SEQUENCE: 14

Glu Leu Thr Phe Thr Pro Gly Trp
1               5

<210> SEQ ID NO 15
<211> LENGTH: 8
<212> TYPE: PRT
<213> ORGANISM: Phymateus leprosus

<400> SEQUENCE: 15
```

```
Glu Leu Asn Phe Ser Thr Gly Trp
1               5

<210> SEQ ID NO 16
<211> LENGTH: 8
<212> TYPE: PRT
<213> ORGANISM: Libellula auripennis

<400> SEQUENCE: 16

Glu Val Asn Phe Thr Pro Ser Trp
1               5

<210> SEQ ID NO 17
<211> LENGTH: 8
<212> TYPE: PRT
<213> ORGANISM: Anax imperator

<400> SEQUENCE: 17

Glu Val Asn Phe Ser Pro Ser Trp
1               5

<210> SEQ ID NO 18
<211> LENGTH: 8
<212> TYPE: PRT
<213> ORGANISM: Blatta orientalis

<400> SEQUENCE: 18

Glu Val Asn Phe Ser Pro Asn Trp
1               5

<210> SEQ ID NO 19
<211> LENGTH: 8
<212> TYPE: PRT
<213> ORGANISM: Blatta orientalis

<400> SEQUENCE: 19

Glu Leu Thr Phe Thr Pro Asn Trp
1               5

<210> SEQ ID NO 20
<211> LENGTH: 8
<212> TYPE: PRT
<213> ORGANISM: Tenebrio molitor

<400> SEQUENCE: 20

Glu Leu Asn Phe Ser Pro Asn Trp
1               5

<210> SEQ ID NO 21
<211> LENGTH: 8
<212> TYPE: PRT
<213> ORGANISM: Polyphaga aegyptiaca

<400> SEQUENCE: 21

Glu Leu Asn Phe Ser Pro Asn Trp
1               5

<210> SEQ ID NO 22
<211> LENGTH: 8
<212> TYPE: PRT
<213> ORGANISM: Polyphaga aegyptiaca

<400> SEQUENCE: 22

Glu Ile Thr Phe Thr Pro Asn Trp
```

```
<210> SEQ ID NO 23
<211> LENGTH: 8
<212> TYPE: PRT
<213> ORGANISM: Empusa pennata

<400> SEQUENCE: 23

Glu Val Asn Phe Thr Pro Asn Trp
1               5

<210> SEQ ID NO 24
<211> LENGTH: 8
<212> TYPE: PRT
<213> ORGANISM: Gryllodes sigillatus

<400> SEQUENCE: 24

Glu Val Asn Phe Ser Thr Gly Trp
1               5

<210> SEQ ID NO 25
<211> LENGTH: 8
<212> TYPE: PRT
<213> ORGANISM: Libanasidus vittatus

<400> SEQUENCE: 25

Glu Leu Asn Phe Ser Thr Gly Trp
1               5

<210> SEQ ID NO 26
<211> LENGTH: 8
<212> TYPE: PRT
<213> ORGANISM: Pseudagrion inconspicuum

<400> SEQUENCE: 26

Glu Val Asn Phe Thr Pro Gly Trp
1               5

<210> SEQ ID NO 27
<211> LENGTH: 8
<212> TYPE: PRT
<213> ORGANISM: Dictiophorus spumans

<400> SEQUENCE: 27

Glu Ile Asn Phe Thr Pro Trp Trp
1               5

<210> SEQ ID NO 28
<211> LENGTH: 8
<212> TYPE: PRT
<213> ORGANISM: Scarabaeus sp.

<400> SEQUENCE: 28

Glu Phe Asn Tyr Ser Pro Asp Trp
1               5

<210> SEQ ID NO 29
<211> LENGTH: 8
<212> TYPE: PRT
<213> ORGANISM: Scarabaeus sp.

<400> SEQUENCE: 29

Glu Phe Asn Tyr Ser Pro Val Trp
1               5
```

```
<210> SEQ ID NO 30
<211> LENGTH: 8
<212> TYPE: PRT
<213> ORGANISM: Onitis sp.

<400> SEQUENCE: 30

Glu Tyr Asn Phe Ser Thr Gly Trp
1               5

<210> SEQ ID NO 31
<211> LENGTH: 8
<212> TYPE: PRT
<213> ORGANISM: Onitis sp.

<400> SEQUENCE: 31

Glu Phe Asn Tyr Ser Pro Asp Trp
1               5

<210> SEQ ID NO 32
<211> LENGTH: 10
<212> TYPE: PRT
<213> ORGANISM: Paltypelura capensis

<400> SEQUENCE: 32

Glu Val Asn Phe Ser Pro Ser Trp Gly Asn
1               5                   10

<210> SEQ ID NO 33
<211> LENGTH: 10
<212> TYPE: PRT
<213> ORGANISM: Extatosoma tiaratum

<400> SEQUENCE: 33

Glu Leu Thr Phe Thr Pro Asn Trp Gly Thr
1               5                   10

<210> SEQ ID NO 34
<211> LENGTH: 10
<212> TYPE: PRT
<213> ORGANISM: Heliothis zea

<400> SEQUENCE: 34

Glu Leu Thr Phe Ser Ser Gly Trp Gly Asn
1               5                   10

<210> SEQ ID NO 35
<211> LENGTH: 10
<212> TYPE: PRT
<213> ORGANISM: Schistocerca gregaria

<400> SEQUENCE: 35

Glu Leu Asn Phe Thr Pro Asn Trp Gly Thr
1               5                   10

<210> SEQ ID NO 36
<211> LENGTH: 10
<212> TYPE: PRT
<213> ORGANISM: Tenthredo arcuata

<400> SEQUENCE: 36

Glu Leu Asn Phe Ser Thr Gly Trp Gly Gly
1               5                   10

<210> SEQ ID NO 37
```

-continued

```
<211> LENGTH: 11
<212> TYPE: PRT
<213> ORGANISM: Vanessa cardui

<400> SEQUENCE: 37

Glu Leu Thr Phe Thr Ser Ser Trp Gly Gly Lys
1               5                   10

<210> SEQ ID NO 38
<211> LENGTH: 8
<212> TYPE: PRT
<213> ORGANISM: Periplaneta americana

<400> SEQUENCE: 38

Glu Leu Thr Phe Thr Pro Asn Trp
1               5

<210> SEQ ID NO 39
<211> LENGTH: 10
<212> TYPE: PRT
<213> ORGANISM: Phymateus leprosus

<400> SEQUENCE: 39

Glu Leu Thr Phe Thr Pro Asn Trp Gly Ser
1               5                   10

<210> SEQ ID NO 40
<211> LENGTH: 10
<212> TYPE: PRT
<213> ORGANISM: Tabanus atratus

<400> SEQUENCE: 40

Glu Leu Thr Phe Thr Pro Gly Trp Gly Tyr
1               5                   10

<210> SEQ ID NO 41
<211> LENGTH: 13
<212> TYPE: PRT
<213> ORGANISM: Insect sp.

<400> SEQUENCE: 41

Ser Tyr Ser Met Glu His Phe Arg Trp Gly Lys Pro Val
1               5                   10

<210> SEQ ID NO 42
<211> LENGTH: 19
<212> TYPE: PRT
<213> ORGANISM: Insect sp.

<400> SEQUENCE: 42

Asp Phe Asp Met Leu Arg Cys Met Leu Gly Arg Val Tyr Arg Pro Cys
1               5                   10                  15

Trp Gln Val
```